United States Patent
Kondo et al.

(10) Patent No.: US 10,351,882 B2
(45) Date of Patent: *Jul. 16, 2019

(54) METHOD FOR PRODUCING AN OIL OR FAT COMPONENT AND METHOD FOR PRODUCING HIGHER UNSATURATED FATTY ACID USING ALGAE

(71) Applicants: National University Corporation Kobe University, Kobe-shi (JP); Inter-University Research Institute Corporation National Institutes of Natural Sciences, Mitaka-shi, Tokyo (JP); DIC Corporation, Tokyo (JP)

(72) Inventors: Akihiko Kondo, Kobe (JP); Tomohisa Hasunuma, Kobe (JP); Shih-hsin Ho, Kobe (JP); Jun Minagawa, Okazaki (JP); Haruo Nishie, Sakura (JP); Hiroyuki Taroda, Sakura (JP); Jo-Shu Chang, Taichung (TW)

(73) Assignees: National University Corporation KOBE University, Kobe-shi (JP); Inter-University Research Institute Corporation National Institutes of Natural Sciences, Tokyo (JP); DIC Corporation, Tokyo (JP)

( * ) Notice: Subject to any disclaimer, the term of this patent is extended or adjusted under 35 U.S.C. 154(b) by 19 days.

This patent is subject to a terminal disclaimer.

(21) Appl. No.: 14/913,618

(22) PCT Filed: Mar. 17, 2014

(86) PCT No.: PCT/JP2014/057177
§ 371 (c)(1),
(2) Date: Feb. 22, 2016

(87) PCT Pub. No.: WO2015/025552
PCT Pub. Date: Feb. 26, 2015

(65) Prior Publication Data
US 2016/0215307 A1 Jul. 28, 2016

(30) Foreign Application Priority Data

Aug. 23, 2013 (JP) .................................. 2013-173417

(51) Int. Cl.
*C12P 7/64* (2006.01)

(52) U.S. Cl.
CPC ............... *C12P 7/6409* (2013.01); *C12P 7/64* (2013.01); *C12P 7/6463* (2013.01); *C12P 7/649* (2013.01)

(58) Field of Classification Search
None
See application file for complete search history.

(56) References Cited

U.S. PATENT DOCUMENTS

2016/0201098 A1  7/2016  Kondo et al.

FOREIGN PATENT DOCUMENTS

| CN | 102453682 A | 5/2012 |
|---|---|---|
| CN | 103146581 A | 6/2013 |
| JP | 07-075557 A | 3/1995 |
| JP | 11-196885 A | 7/1999 |
| JP | 2000-316593 A | 11/2000 |
| JP | 3837589 B2 | 10/2006 |
| JP | 4081794 B2 | 4/2008 |
| JP | 2009-060876 A | 3/2009 |
| JP | 2013-102748 A | 5/2013 |

OTHER PUBLICATIONS

Al Hasan et al., Journal of General Microbiology (1987), 133, 2607-2616.*
Lu et al., Process Biochemistry, vol. 47, 2012, pp. 1163-1170).*
M.Takagi et al., "Effect of Salt Concentration on Intracellular Accumulation of Lipids and Triacylglyceride in Marine Microalgae *Dunaliella* Cells," Journal of Bioscience and Bioengineering,vol. 101, 2006, pp. 223-226.
Y. Collos et al., "An optical method for the rapid measurement of micromolar concentrations of nitrate in marine phytoplankton cultures," Journal of Applied Phycology,vol. 11, 1999, pp. 179-184.
M.Siaut et al., "Oil accumulation in the model green alga *Chlamydomonas reinhardtii*: characterization, variability between common laboratory strains and relationship with starch reserves," BMC Biotechnology, vol. 11, No. 7, 2011, pp. 1-15.
A. R. Rao et al., "Effect of salinity on growth of green alga *Botryococcus braunii* and its constituents," Bioresource Technology, vol. 98, 2007, pp. 560-564.
A. Nakanishi et al., "Development of high lipid producing system by green alga *Chlamydomonas orbicularis* under sea salt condition," Abstracts of the Annual meeting of the society for Biotechnology, Japan, vol. 65, Aug. 25, 2013, p. 64 (1P-185).
E. S. Salama et al., "Biomass, lipid content, and fatty acid composition of freshwater *Chlamydomonas mexicana* and *Scenedesmus obliquus* grown under salt stress," Bioprocess Biosyst. Eng, vol. 36, 2013, pp. 827-833.
S.-H. Ho et al., "Phototrophic cultivation of a marine microalga *Chlamydomonas orbicularis* for $CO_2$ fixation and biodiesel production: Effect of medium composition, nitrogen depletion, and sea salt concentration," Abstracts of the Annual meeting of the society for Biotechnology, Japan, vol. 65, Aug. 25, 2013, p. 66 (1P-196).
A. Nakanishi et al., "Development of lipid productivities under different $CO_2$ conditions of marine microalgae *Chlamydomonas* sp. JSC4," Bioresource Technology, vol. 152, 2014, pp. 247-252.
International Search Report dated Apr. 28, 2014, issued for PCT/JP2014/057177 and English translation thereof.

(Continued)

*Primary Examiner* — Michelle F. Paguio Frising
(74) *Attorney, Agent, or Firm* — Locke Lord LLP

(57) ABSTRACT

There is provided a method for generating an oil/fat component, in which salt-tolerant algae are cultured in a culture medium of which the salt concentration has been increased in a stepwise manner.

13 Claims, 15 Drawing Sheets

Specification includes a Sequence Listing.

(56) References Cited

OTHER PUBLICATIONS

International Search Report dated Jun. 17, 2014, issued for PCT/JP2014/057185 and English translation thereof.
Shih-Hsin Ho et al., "Optimizing biodiesel production in marine *Chlamydomonas* sp. JSC4 through metabolic profiling and an innovative salinity-gradient strategy," Biotechnology for Biofuels, Biomed Central Ltd, GB, vol. 7, No. 1, Jun. 24, 2014, p. 97 (16 pages). (cited in the Mar. 17, 2017 EP OA).
Office Action dated Mar. 7, 2017, issued for U.S. Appl. No. 14/913,594.
Supplementary European Search Report dated Mar. 17, 2017, issued for the European patent application No. 14837252.7.
Office Action dated on Mar. 1, 2018 issued for corresponding European Patent Application No. 14 838 058.7.
Meiling AN et al: "Expression of fatty acid desaturase genes and fatty acid accumulation in *Chlamydomonas* sp. ICE-L under salt stress", Bioresource Technology, vol. 149, pp. 77-83 (2013).
Anonymous: "Sea salt", Wikipedia, the free encyclopedia, Aug. 13, 2013, XP002765650, Retrieved from the Internet: URL: <https://web.archive.org/web/20130813030057/http://en.wikipedia.org/wiki/Sea_Salt> [retrieved on Jan. 4, 2017] (cited in the Jan. 25, 2017 EP Search Report).
Greenbaum E et al: "Hydrogen and Oxygen Photo Production by Marine Algae", Photochemistry and Photobiology, vol. 37, No. 6, Jun. 1, 1983, pp. 649-656. (cited in the Jan. 25, 2017 EP Search Report).
Search Report dated Jan. 25, 2017, issued for the European Patent Application No. 14838058.7.
Office Action dated Mar. 15, 2019, issued for the Chinese patent application No. 201480057778.4 and a partial translation of the Search Report.

* cited by examiner

FIG. 2

```
                                 1                                                          50
Chlamydomonas sp. JSC4           TAC-TTAGCA TGGAATAACA CGATAGGACT CTGGCCTATC T-GTTGGTCT
Chlamydomonas debaryana          TACATTAGCA TGGAATAACA CGATAGGACT CTGGCCTATC T-GTTGGTCT
Chlamydomonas cribrum            TACATTAGCA TGGAATAACA CGATAGGACT CTGGCCTATC T-GTTGGTCT
Chlamydomonas incerta            TACATTAGCA TGGAATAACA CGATAGGACT CTGGCCTATC T-GTTGGTCT
Chlamydomonas reinhardtii        TACATTAGCA TGGAATAACA CGATAGGACT CTGGCCTATC T-GTTGGTCT
Chlamydomonas zebra              TACATTAGCA TGGAATAACA CGATAGGACT CTGGCCTATC T-GTTGGTCT
Chlamydomonas oogama             TACATTAGCA TGGAATAACA CGATAGGACT CTGGCCTATC T-GTTGGTCT
Chlamydomonas longispicula       TACGTTAGCA TGGAATAACA TGATAGGACT CTGGCCTATC TTGTTGGTCT
Chlamydomonas pseudovolvox       TACATTAGCA TGGAATAACA CGATAGGACT CTGGCCTATC T-GTTGGTCT
Chlamydomonas sociale            TACATTAGCA TGGAATAACA TGATAGGACT CTGGCCTATC T-GTTGGTCT
Chlamydomonas carteri            TACATTAGCA TGGAATAACA CGATAGGACT CTGGCCTATC T-GTTGGTCT 51                                                         100
Chlamydomonas sp. JSC4           GTGGGACCGG AGTAATGATT AAGAGGGGTA GGCGGGGGCA TTCGTATCCC
Chlamydomonas debaryana          GTGGGACCGG AGTAATGATT AAGAGGGGTA GTCGGGGGCA TTCGTATTCC
Chlamydomonas cribrum            GTGGGACCGG AGTAATGATT AAGAGGGGTA GTCGGGGGCA TTCGTATTGC
Chlamydomonas incerta            GTGGGACCGG AGTAATGATT AAGAGGGGTA GTCGGGGGCA TTCGTATTCC
Chlamydomonas reinhardtii        GTGGGACCGG AGTAATGATT AAGAGGGGTA GTCGGGGGCA TTCGTATTCC
Chlamydomonas zebra              GTGGGACTGG AGTAATGATT AAGAGGGGTA GTCGGGGGCA TTCGTATTCC
Chlamydomonas oogama             GTGGGACCGG AGTAATGATT AAGAGGGGTA GTCGGGGGCA TTCGTATTCC
Chlamydomonas longispicula       GTAGGACTGG AGTAATGATT AAGAGGGACA GTCGGGGGCA TTCGTATTGC
Chlamydomonas pseudovolvox       GTGGGACCGG AGTAATGATT AAGAGGGACA GTCGGGGGCA TTCGTATTCC
Chlamydomonas sociale            GTGGGACCGG AGTAATGATT AAGAGGGGTA GTCGGGGGCA TTCGTATTCC
Chlamydomonas carteri            GTGGGATCGG AGTAATGATT AAGAGGGGTA GTCGGGGGCA TTCGTATTCC 101                                                        150
Chlamydomonas sp. JSC4           GTTGTCAGAG GTGAGATTCT TGGATGTACG GAAGACAAAC ATCTGCGAAA
Chlamydomonas debaryana          GTTGTCAGAG GTGAAATTCT TGGATTTACG GAAGACGAAC ATNTGCGAAA
Chlamydomonas cribrum            GTTGTCAGAG GTGAAATTCT TGGATTTACG CAAGACGAAC ATCTGCGAAA
Chlamydomonas incerta            GTTGTCAGAG GTGAAATTCT TGGATTTACG GAAGACGAAC ATCTGCGAAA
Chlamydomonas reinhardtii        GTTGTCAGAG GTGAAATTCT TGGATTTACG GAAGACGAAC ATCTGCGAAA
Chlamydomonas zebra              GTTGTCAGAG GTGAAATTCT TGGATTTACG GAAGACGAAC ATCTGCGAAA
Chlamydomonas oogama             GTTGTCAGAG GTGAAATTCT TGGATTTACG GAAGACGAAC ATCTGCGAAA
Chlamydomonas longispicula       GCTGTCAGAG GTGAAATTCT TGGATTTGCG CAAGACGAAC ATCTGCGAAA
Chlamydomonas pseudovolvox       ATTGTCAGAG GTGAAATTCT TGGATTTATG GAAGACGAAC ATCTGCGAAA
Chlamydomonas sociale            GTTGTCAGAG GTGAAATTCT TGGATTTACG GAAGACGAAC ATCTGCGAAA
Chlamydomonas carteri            GTTGTCAGAG GTGAAATTCT TGGATTTACG GAAGACGAAC ATCTGCGAAA 151                                                        200
Chlamydomonas sp. JSC4           GCATTTGCCA AGGATACTTT CATTGATCAA G-----GGGT TGGGGGCTTG
Chlamydomonas debaryana          GCATTTGCCA AGGATACTTT CATTGATCAA GAACGAAAGT TGGGGGCTCG
Chlamydomonas cribrum            GCATTTGCCA AGGATACTTT CATTGATCAA GAACGAAAGT TGGGGGCTCG
Chlamydomonas incerta            GCATTTGCCA AGGATACTTT CATTGATCAA GAACGAAAGT TGGGGGCTCG
Chlamydomonas reinhardtii        GCATTTGCCA AGGATACTTT CATTGATCAA GAACGAAAGT TGGGGGCTCG
Chlamydomonas zebra              GCATTTGCCA AGGATACTTT CATTGATCAA GAACGAAAGT TGGGGGCTCG
Chlamydomonas oogama             NCATTTGCCA AGGATACTTT CATTGATCAA GAACGAAAGT TGGGGGCTCG
Chlamydomonas longispicula       GCATTTGCCA AGGATGTTTT CATTGATCAA GAACGAAAGT TGGGGGCTCG
Chlamydomonas pseudovolvox       GCATTTGCCA AGGATGTTTC -ATTGATCAA GAACGAAAGT TGGGGGCTCG
Chlamydomonas sociale            GCATTTGCCA AGGATACTTT CATTGATCAA GAACGAAAGT TGGGGGCTCG
Chlamydomonas carteri            GCATTTGCCA AGGATACTTT CATTGATCAA GAACGAAAGT TGGGGGCTCG
```

FIG. 3

```
                               201                                                          250
Chlamydomonas sp. JSC4         AAGACGGTTA GATACCGTCG TAGTCTCAAC CATAAACGAT GCCGACTAGG
Chlamydomonas debaryana        AAGACGATTA GATACCGTCG TAGTCTCAAC CATAAACGAT GCCGACTAGG
Chlamydomonas cribrum          AAGACGATTA GATACCGTCG TAGTCTCAAC CATAAACGAT GCCGACTAGG
Chlamydomonas incerta          AAGACGATTA GATACCGTCG TAGTCTCAAC CATAAACGAT GCCGACTAGG
Chlamydomonas reinhardtii      AAGACGATTA GATACCGTCG TAGTCTCAAC CATAAACGAT GCCGACTAGG
Chlamydomonas zebra            AAGACGATTA GATACCGTCG TAGTCTCAAC CATAAACGAT GCCGACTAGG
Chlamydomonas oogama           AAGACGATTA GATACCGTCG TAGTCTCAAC CATAAACGAT GCCGACTAGG
Chlamydomonas longispicula     AAGACGATTA GATACCGTCG TAGTCTCAAC CATAAACGAT GCCGACTAGG
Chlamydomonas pseudovolvox     AAGACGATTA GATACCGTCG TAGTCTCAAC CATAAACGAT GCCGACTAGG
Chlamydomonas sociale          AAGACGATTA GATACCGTCG TAGTCTCAAC CATAAACGAT GCCGACTAGG
Chlamydomonas carteri          AAGACGATTA GATACCGTCG TAGTCTCAAC CATAAACGAT GCCGACTAGG 251                                                          300
Chlamydomonas sp. JSC4         GATTGGCAGA TGTTCCTTTG ATGACTCTGC CAGCACCTTA TAAGGAATCA
Chlamydomonas debaryana        GATTGGCAGA TGTTCCTTTG ATGACTCTGC CAGCACCTTA TGAGAAATCA
Chlamydomonas cribrum          GATTGGCGGA TGTTCCTTTG ATGACCCCGC CAGCACCTTA TGAGAAATCA
Chlamydomonas incerta          GATTGGCAGA TGTTCTTTTG ATGACTCTGC CAGCACCTTA TGAGAAATCA
Chlamydomonas reinhardtii      GATTGGCAGA TGTTCTTTTG ATGACTCTGC CAGCACCTTA TGAGAAATCA
Chlamydomonas zebra            GATTGGCGGA TGTTCTTTTG ATGACTCCGC CAGCACCTTA TGAGAAATCA
Chlamydomonas oogama           GATTGGCAGA TGTTCCTTTA ATGACTCTGC CAGCACCTTA TGAGAAATCA
Chlamydomonas longispicula     GATTGGTGGG AGTTTCTTCG ATGACTCCGC CAGCACCTTA TGAGAAATCA
Chlamydomonas pseudovolvox     GATTGGCAGA TGTTCCATTG ATGACTCTGC CAGCACCTTA TGAGAAATCA
Chlamydomonas sociale          GATTGGCAGA TGTTCCTTTG ATGACTCTGC CAGCACCTTA TGAGAAATCA
Chlamydomonas carteri          GATTGGCAGA TGTTCTTTTG ATGACTCTGC CAGCACCTTA TGAGAAATCA 301                                                          350
Chlamydomonas sp. JSC4         AAGTTTTTGG GTTCCGGGGG GAGTATGGTC ACAACGCTGA AACTTGAAGG
Chlamydomonas debaryana        AAGTTTTTGG GTTCCGGGGG GAGTATGGTC GCAAGGCTGA AACTTAAAGG
Chlamydomonas cribrum          AAGTTTTTGG GTTCCGGGGG GAGTATGGTC GCAAGGCTGA AACTTAAAGG
Chlamydomonas incerta          AAGTTTTTGG GTTCCGGGGG GAGTATGGTC GCAAGGCTGA AACTTAAAGG
Chlamydomonas reinhardtii      AAGTTTTTGG GTTCCGGGGG GAGTATGGTC GCAAGGCTGA AACTTAAAGG
Chlamydomonas zebra            AAGTTTTTGG GTTCCGGGGG GAGTATGGTC GCAAGGCTGA AACTTAAAGG
Chlamydomonas oogama           AAGTTTTTGG GTTCCGGGGG GAGTATGGTC GCAAGGCTGA AACTTAAAGG
Chlamydomonas longispicula     AAGTCTCTGG GTTCCGGGGG GAGTATGGTC GCAAGGCTGA AACTTAAAGG
Chlamydomonas pseudovolvox     AAGTTTTTGG GTTCCGGGGG GAGTATGGTC GCAAGGTTGA AACTTAAAGG
Chlamydomonas sociale          AAGTTTTTGG GTTCCGGGGG GAGTATGGTC GCAAGGCTGA AACTTAAAGG
Chlamydomonas carteri          AAGTTTTTGG GTTCCGGGGG GAGTATGGTC GCAAGGCTGA AACTTAAAGG 351                                                          400
Chlamydomonas sp. JSC4         AATTGACGGA AGGGCACCAC CAGGGCCACA AGCCTGCGGC TTAATTTGTC
Chlamydomonas debaryana        AATTGACGGA AGGGCACCAC CAGGCGTGG- AGCCTGCGGC TTAATTTGAC
Chlamydomonas cribrum          AATTGACGGA AGGGCACCAC CAGGCGTGG- AGCCTGCGGC TTAATTTGAC
Chlamydomonas incerta          AATTGACGGA AGGGCACCAC CAGGCGTGG- AGCCTGCGGC TTAATTTGAC
Chlamydomonas reinhardtii      AATTGACGGA AGGGCACCAC CAGGCGTGG- AGCCTGCGGC TTAATTTGAC
Chlamydomonas zebra            AATTGACGGA AGGGCACCAC CAGGCGTGG- AGCCTGCGGC TTAATTTGAC
Chlamydomonas oogama           AATTGACGGA AGGGCACCAC CAGGCGTGG- AGCCTGCGGC TTAATTTGAC
Chlamydomonas longispicula     AATTGACGGA AGGGCACCAC CAGGCGTGG- AGCCTGCGGC TTAATTTGAC
Chlamydomonas pseudovolvox     AATTGACGGA AGGGCACCAC CAGGCGTGG- AGCCTGCGGC TTAATTTGAC
Chlamydomonas sociale          AATTGACGGA AGGGCACCAC CAGGCGTGG- AGCCTGCGGC TTAATTTGAC
Chlamydomonas carteri          AATTGACGGA AGGGCACCAC CAGGCGTGG- AGCCTGCGGC TTAATTTGAC
```

FIG. 4

```
                              401                                                           450
Chlamydomonas sp. JSC4        TCAACACGGG GAAACTTACC AGGTCCAGAC ACGGGAAGGA TTGACAGATT
Chlamydomonas debaryana       TCAACACGGG GAAACTTACC AGGTCCAGAC ACGGGAAGGA TTGACAGATT
Chlamydomonas cribrum         TCAACACGGG GAAGCTTACC AGGTCCAGAC ACGGGAAGGA CTGACAGATT
Chlamydomonas incerta         TCAACACGGG GAAACTTACC AGGTCCAGAC ACGGGAAGGA TTGACAGATT
Chlamydomonas reinhardtii     TCAACACGGG GAAACTTACC AGGTCCAGAC ACGGGAAGGA TTGACAGATT
Chlamydomonas zebra           TCAACACGGG GAAACTTACC AGGTCCAGAC ACGGGAAGGA TTGACAGATT
Chlamydomonas oogama          TCAACACGGG GAAACTTACC AGGTCCAGAC ACGGGAAGGA TTGACAGATT
Chlamydomonas longispicula    TCAACACGGG AAAACTTACC AGGTCCAGAC ACAGGGAGGA TTGACAGATT
Chlamydomonas pseudovolvox    TCAACACGGG GAAACTTACC AGGTCCAGAC ACGGGAAGGA TTGACAGATT
Chlamydomonas sociale         TCAACACGGG GAAACTTACC AGGTCCAGAC ACGGGAAGGA TTGACAGATT
Chlamydomonas carteri         TCAACACGGG GAAACTTACC AGGTCCAGAC ACGGGAAGGA TTGACAGATT 451                                                           500
Chlamydomonas sp. JSC4        GAGAGCTCTT TCTTAATTCT GTGGGTCGTG GTGCATGGCC GTTCTTAGTT
Chlamydomonas debaryana       GAGAGCTCTT TCTTGATTCT GTGGGTGGTG GTGCATGGCC GTTCTTAGTT
Chlamydomonas cribrum         GAGAGCTCTT TCTTGATTCT GTGGGTGGTG GTGCATGGCC GTTCTTAGTT
Chlamydomonas incerta         GAGAGCTCTT TCTTGATTCT GTGGGTGGTG GTGCATGGCC GTTCTTAGTT
Chlamydomonas reinhardtii     GAGAGCTCTT TCTTGATTCT GTGGGTGGTG GTGCATGGCC GTTCTTAGTT
Chlamydomonas zebra           GAGAGCTCTT TCTTGATTCT GTGGGTGGTG GTGCATGGCC GTTCTTAGTT
Chlamydomonas oogama          GAGAGCTCTT TCTTGATTCT GTGGGTGGTG GTGCATGGCC GTTCTTAGTT
Chlamydomonas longispicula    GAGAGCTCTT TCTTGATTCT GTGGGTGGTG GTGCATGGCC GTTCTTAGTT
Chlamydomonas pseudovolvox    GAGAGCTCTT TCTTGATTCT GTGGGTGGTG GTGCATGGCC GTTCTTAGTT
Chlamydomonas sociale         GAGAGCTCTT TCTTGATTCT GTGGGTGGTG GTGCATGGCC GTTCTTAGTT
Chlamydomonas carteri         GAGAGCTCTT TCTTGATTCT GTGGGTGGTG GTGCATGGCC GTTCTTAGTT 501
Chlamydomonas sp. JSC4        GG
Chlamydomonas debaryana       GG
Chlamydomonas cribrum         GG
Chlamydomonas incerta         GG
Chlamydomonas reinhardtii     GG
Chlamydomonas zebra           GG
Chlamydomonas oogama          GG
Chlamydomonas longispicula    GG
Chlamydomonas pseudovolvox    GG
Chlamydomonas sociale         GG
Chlamydomonas carteri         GG
```

| | Fatty acid composition (%) | | |
|---|---|---|---|
| | 2.0% sea salt condition | | SBO-based biodiesel |
| | Nitrogen rich | Nitrogen depletion | |
| Palmitic acid (C16:0) | 25.8 ± 0.6 | 27.6 ± 0.3 | 10.7 |
| Palmitoletic acid (C16:1) | 1.1 ± 0.0 | 3.2 ± 0.1 | 0 |
| Stearic acid (C18:0) | 4.0 ± 1.5 | 3.1 ± 0.1 | 4.4 |
| Oletic acid (C18:1) | 9.1 ± 0.0 | 26.6 ± 0.6 | 23.3 |
| Linoleic acid (C18:2) | 21.7 ± 0.0 | 25.3 ± 0.3 | 54.1 |
| Linolenic acid (C18:3) | 14.4 ± 0.4 | 5.4 ± 0.1 | 7.5 |
| Saturated fatty acid (SFA) | 28.3 ± 0.3 | 30.7 ± 0.5 | 15.1 |
| Monounsaturated fatty acid (MUFA) | 9.8 ± 0.4 | 29.7 ± 0.5 | 23.3 |
| Polyunsaturated fatty acid (PUFA) | 35.0 ± 0.9 | 30.7 ± 0.4 | 61.6 |
| C16 & C18 groups | 76.0 ± 0.5 | 91.1 ± 1.3 | 100 |

FIG. 14

| Being transferred condition of sea salt (%) | Cultivation time under nitrogen depletion (d) | Biomass concentration (g L$^{-1}$) | Lipid content (%) | Lipid productivity (mgL$^{-1}$d$^{-1}$) | CO2 fixation rate (mg L$^{-1}$d$^{-1}$) |
|---|---|---|---|---|---|
| 2% sea salt (Batch) | 3 | 2.232 ± 0.007 | 41.9 ± 1.8 | 158.9 ± 7.6 | 730.9 ± 2.8 |
| | 5 | 2.467 ± 0.064 | 49.8 ± 2.3 | 151.8 ± 11.1 | 560.5 ± 15.6 |
| | 7 | 2.488 ± 0.044 | 53.5 ± 0.8 | 130.0 ± 4.3 | 465.5 ± 8.6 |
| 3% | 3 | 2.141 ± 0.007 | 46.1 ± 1.3 | 183.9 ± 4.6 | 750.4 ± 2.5 |
| | 5 | 2.337 ± 0.009 | 53.8 ± 1.5 | 159.0 ± 4.9 | 555.9 ± 1.7 |
| | 7 | 2.431 ± 0.042 | 56.0 ± 1.0 | 135.7 ± 0.0 | 455.8 ± 8.1 |
| 5% | 3 | 1.796 ± 0.026 | 51.2 ± 1.1 | 169.9 ± 0.9 | 623.4 ± 9.6 |
| | 5 | 1.941 ± 0.010 | 58.2 ± 1.5 | 141.7 ± 4.4 | 457.6 ± 2.3 |
| | 7 | 2.022 ± 0.030 | 61.2 ± 1.8 | 122.4 ± 5.6 | 375.8 ± 5.9 |
| 7% | 3 | 1.593 ± 0.027 | 47.1 ± 0.6 | 137.5 ± 3.7 | 549.1 ± 7.6 |
| | 5 | 1.683 ± 0.013 | 53.3 ± 2.8 | 111.8 ± 6.9 | 394.3 ± 5.5 |
| | 7 | 1.735 ± 0.028 | 57.6 ± 3.0 | 98.0 ± 6.8 | 319.9 ± 5.4 |

FIG. 18

| Sea salt addition (% d⁻¹) | Cultivation time under nitrogen depletion (d) | Biomass concentration (g L⁻¹) | Lipid content (%) | Lipid productivity (mgL⁻¹d⁻¹) | $CO_2$ fixation rate (mg L⁻¹d⁻¹) |
|---|---|---|---|---|---|
| 2% sea salt (Batch) | 0 | 1.426 ± 0.008 | 15.8 ± 0.1 | 110.7 ± 0.2 | 1319.0 ± 6.4 |
|  | 3 | 2.232 ± 0.007 | 41.9 ± 1.8 | 158.9 ± 7.6 | 730.9 ± 2.8 |
|  | 5 | 2.467 ± 0.064 | 49.8 ± 2.3 | 151.8 ± 11.1 | 560.5 ± 15.6 |
| 0.5% | 0 | 1.471 ± 0.010 | 15.3 ± 0.3 | 100.9 ± 2.7 | 1243.0 ± 9.2 |
|  | 3 | 2.129 ± 0.004 | 59.4 ± 0.7 | 223.2 ± 2.1 | 706.4 ± 1.1 |
|  | 5 | 2.180 ± 0.042 | 63.7 ± 0.8 | 174.7 ± 3.3 | 515.3 ± 3.4 |
| 1.0% | 0 | 1.445 ± 0.021 | 15.7 ± 0.6 | 101.6 ± 5.4 | 1218.8 ± 18.8 |
|  | 3 | 2.044 ± 0.015 | 60.2 ± 2.5 | 216.6 ± 7.4 | 676.9 ± 5.3 |
|  | 5 | 2.082 ± 0.079 | 64.9 ± 2.7 | 169.7 ± 13.8 | 491.2 ± 19.6 |
| 1.5% | 0 | 1.436 ± 0.007 | 15.5 ± 0.6 | 99.5 ± 3.4 | 1210.9 ± 6.2 |
|  | 3 | 2.009 ± 0.001 | 53.7 ± 2.0 | 189.8 ± 7.0 | 664.8 ± 0.0 |
|  | 5 | 2.044 ± 0.090 | 59.4 ± 0.3 | 152.1 ± 6.3 | 481.7 ± 22.3 |

FIG. 19

|  | Chlamydomonas sp. JSC4 based FAME composition | | |
|---|---|---|---|
|  | Batch | Two-stage | Salinity-gradient |
| Palmitic acid (C16:0) | 27.6 ± 0.3 | 30.7 ± 0.8 | 30.7 ± 0.5 |
| Palmitoletic acid (C16:1) | 3.2 ± 0.1 | 2.9 ± 0.1 | 2.7 ± 0.2 |
| Stearic acid (C18:0) | 3.1 ± 0.1 | 2.8 ± 0.2 | 2.6 ± 0.2 |
| Oletic acid (C18:1) | 26.6 ± 0.6 | 23.4 ± 0.1 | 22.8 ± 1.1 |
| Linoleic acid (C18:2) | 25.3 ± 0.3 | 25.1 ± 0.1 | 25.0 ± 0.3 |
| Linolenic acid (C18:3) | 5.4 ± 0.1 | 5.0 ± 0.1 | 5.4 ± 0.4 |
| C16&C18 groups | 91.1 ± 1.3 | 89.9 ± 0.8 | 89.7 ± 0.4 |
| Lipid content (%) | 41.9 ± 1.8 | 46.1 ± 1.3 | 59.4 ± 0.7 |
| Lipid productivity (mg $L^{-1}d^{-1}$) | 158.9 ± 7.6 | 183.9 ± 4.6 | 223.2 ± 2.1 |

METHOD FOR PRODUCING AN OIL OR FAT COMPONENT AND METHOD FOR PRODUCING HIGHER UNSATURATED FATTY ACID USING ALGAE

CROSS REFERENCE TO RELATED APPLICATIONS

This application is related to co-pending application: "METHOD FOR GENERATING OIL/FAT COMPONENT, METHOD FOR PRODUCING HIGHER UNSATURATED FATTY ACID, AND *CHLAMYDOMONAS* SP. JSC4" filed even date herewith in the names of Akihiko KONDO, Tomohisa HASUNUMA, Shih-hsin HO, Jun MINAGAWA, Haruo NISHIE, Hiroyuki TARODA, Jo-Shu CHANG as a national phase entry of PCT/JP2014/057185 filed on Mar. 17, 2014, which application is assigned to the assignee of the present application and is incorporated by reference herein.

TECHNICAL FIELD

The present invention relates to a method for generating an oil/fat component which is useful as a fuel or a chemical raw material and particularly relates to a method for generating an oil/fat component, in which salt-tolerant algae are cultured in a culture medium of which the salt concentration has been increased in a stepwise manner.

BACKGROUND ART

Photosynthetic organisms are used as a general term of organisms that fix $CO_2$ using light energy and particularly an alga indicates a kind of photosynthetic organism with high photosynthetic efficiency under excellent culture conditions. Since, the industrial cultivation of algae has been performed for more than half a century and there has been a demand for algae to be used as industrial raw materials, fuels, feed and raw materials of fine chemicals, and health food, it is considered that the algae production occupies an important place in the future of industry.

Since various useful carbon components are generated through the process of fixation of $CO_2$, in the process of culturing algae, algae culture and the research on production of various carbon components through the culture have been actively conducted.

In the future, the need for early search for alternative fuels has been increased from the concern that fossil fuels are depleted and a demand for functional chemicals preferable for maintaining and improving health is increased due to an increase in health-oriented consumers. Therefore, there has been a growing interest in the useful components generated from algae.

In the related art, as an example of a method for producing a carbon component using algae, PTL 1 describes, as a production of ethanol useful for fuels or raw chemical materials, microalgae *Chlamydomonas* sp. MT-JE-SH-1 belonging to *Chlamydomonas* that produces ethanol from starch in cells by being grown at the salt concentration of seawater, accumulating starch in cells, and maintaining the cells under the dark and anaerobic atmosphere. As the means for solving the above-described problem, PTL 1 also describes a method for generating ethanol by culturing (1) microalgae *Chlamydomonas* sp. MT-JE-SH-1 belonging to *Chlamydomonas* that produces ethanol from starch in cells by being grown at the salt concentration of seawater, accumulating starch in cells, and maintaining the cells under the dark and anaerobic atmosphere and (2) microalgae *Chlamydomonas* sp. MT-JE-SH-1 belonging to *Chlamydomonas* at the salt concentration of seawater, accumulating starch in cells, and maintaining a slurry that contains the cultured alga body under the dark and anaerobic atmosphere while the pH thereof is maintained in the range of 6.0 to 9.0.

Further, as a method for producing an oil/fat component, PTL 2 describes a method for culturing a microorganism, that is, 4,7,10,13,16-docosapentaenoic acid-producing bacteria strain L59 (PERM P-18987) belonging to *Labyrinthula* in the Labyrinthulaceae, accumulating oils and fats containing 4,7,10,13,16-docosapentaenoic acid as a constituent fatty acid in bacterial cells, separating the bacterial cells, extracting the oils and fats from the separated bacterial cells using a solvent, and hydrolyzing the extract.

In NPL 1, the relation between generating oils and fats using marine algae and the salt concentration at the time of cultivation is examined and NPL 1 describes that the growth of algae is suppressed in a case where the initial concentration of the salt concentration exceeds 1.5 M and a high lipid content are generated in a case where the initial concentration thereof is in the range of 0.5 M to 1.0 M.

CITATION LIST

Patent Literature

[PTL 1] Japanese Patent No. 3837589
[PTL 2] Japanese Patent No. 4081794

Non-Patent Literature

[NPL 1] Journal of Bioscience and Bioengineering, Vol. 101, pp. 223 to 226 (2006)

SUMMARY OF INVENTION

Technical Problem

In the above-described background art, even though a useful carbon component is generated from algae, the carbon component has low production efficiency and does not fully meet the demands of customers. Therefore, provision of a method for generating a useful carbon component using algae with high production efficiency has been awaited.

Here, in consideration of the above-described background art, an object of the present invention is to provide a method for generating a useful carbon component with high efficiency using algae.

Solution to Problem

In order to solve the above-described problems, the present inventors conducted intensive research on a method for culturing algae, and solved the problem.

That is, in the present invention, the above-described problem is solved by means of providing a method for generating an oil/fat component described below.

[1] A method for generating an oil/fat component, the method including: culturing salt-tolerant algae in a culture medium of which the salt concentration has been increased in a stepwise manner.

[2] The method for generating an oil/fat component according to [1], in which salt-tolerant algae are cultured in a culture medium of which the salt concentration has been increased by 0.5% to 5% in a stepwise manner.

[3] The method for generating an oil/fat component according to [1] or [2], in which salt-tolerant algae are cultured in a culture medium of which the salt concentration has been increased by 0.5% to 2% per day in a stepwise manner.

[4] The method for generating an oil/fat component according to any one of [1] to [3], in which the salt concentration of a culture medium in the first stage is in the range of 0.5% by mass to 5% by mass.

[5] The method for generating an oil/fat component according to any one of [1] to [4], further including: performing cultivation under the condition in which the nitrogen content is low.

[6] The method for generating an oil/fat component according to any one of [1] to [5], further comprising: increasing the salt concentration in the second stage when the content of nitrate in the culture medium becomes 10 mg/L or less in a case where the content thereof at a wavelength of 220 nm is measured.

[7] The method for generating an oil/fat component according to any one of [1] to [6], in which the salt-tolerant algae are algae belonging to *Chlamydomonas*.

[8] The method for generating an oil/fat component according to any one of [1] to [7], in which the salt-tolerant algae are *Chlamydomonas* sp. JSC4.

[9] The method for generating an oil/fat component according to any one of [1] to [8], in which the culture medium contains seawater, concentrated seawater, or artificial seawater.

[10] A method for producing a higher unsaturated fatty acid, the method including: hydrolyzing an oil/fat component obtained by the method for generating an oil/fat component according to any one of [1] to [9].

[11] The method for producing a higher unsaturated fatty acid according to [10], in which the higher unsaturated fatty acid is oleic acid or linolenic acid.

Advantageous Effects of Invention

According to the present invention, it is possible to provide a method for producing a useful carbon component with high efficiency using algae.

BRIEF DESCRIPTION OF DRAWINGS

FIG. 2 shows comparison of 18S rDNA sequences of closely related *Chlamydomonas* species.

FIG. 3 shows comparison of 18S rDNA sequences of closely related *Chlamydomonas* species.

FIG. 4 shows comparison of 18S rDNA sequences of closely related *Chlamydomonas* species.

FIG. 14 shows results of time course profiles of the biomass concentration, the lipid content, the lipid productivity, and the $CO_2$ fixation rate obtained by culturing *Chlamydomonas* sp. JSC4 according to the two-stage culture method.

FIG. 18 shows results of time course profiles of the biomass concentration, the lipid content, the lipid productivity, and the $CO_2$ fixation rate obtained by culturing *Chlamydomonas* sp. JSC4 according to the gradient method.

FIG. 19 shows results of analyzing compositions of fatty acids of *Chlamydomonas* sp. JSC4 cultured according to the respective methods.

DESCRIPTION OF EMBODIMENTS

[Salt-Tolerant Algae]

Figure 1:
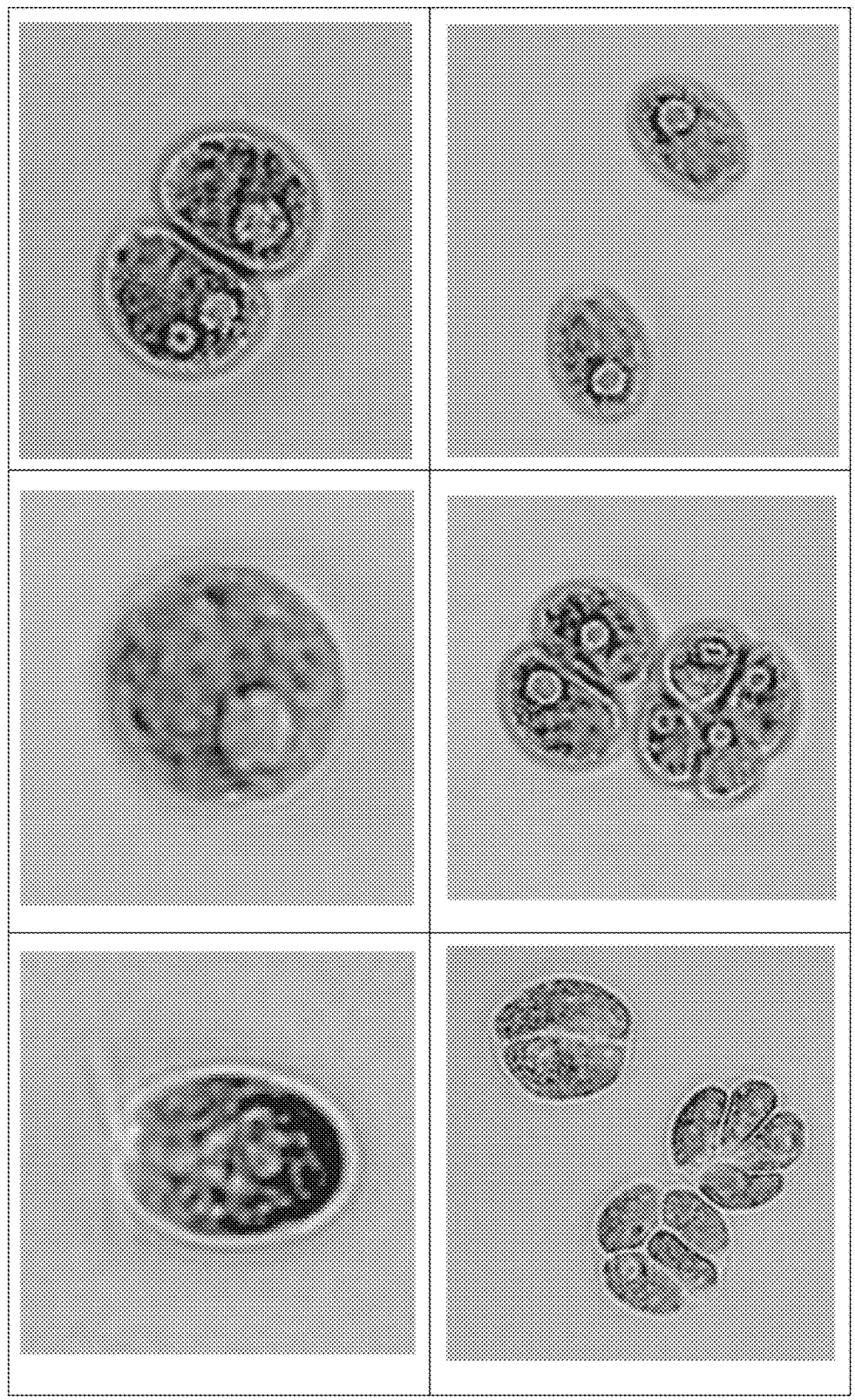
FIG. 1 is a micrograph of vegetative cells (cells which vigorously grow in a suitable growing environment and under the rich nutrient conditions) of *Chlamydomonas* sp. JSC4.

Algae used in the present invention are not limited as long as the algae are salt-tolerant, and examples thereof include algae belonging to *Chlamydomonas*, algae belonging to *Chlorella*, algae belonging to *Dunaliella*, algae belonging to *Nannochloropsis*, algae belonging to *Botryococcus*, algae belonging to *Chaetoceros*, algae belonging to *Chlorecoccum*, algae belonging to *Euglena*, algae belonging to *Haematococcus*, algae belonging to *Isochrysis*, algae belonging to *Naviculaa*, algae belonging to *Neochloris*, algae belonging to *Porphyridium*, algae belonging to *Prymnesium*, algae belonging to *Scenedes*, algae belonging to *Spirulina*, algae belonging to *Spirogyra*, algae belonging to *Synechoccus*, and algae belonging to *Tetraselmis*. Among these, algae belonging to *Chlamydomonas*, algae belonging to *Chlorella*, algae belonging to *Dunaliella*, and algae belonging to *Nannochloropsis* are preferable.

*Chlamydomonas* is a genus consisting of unicellular flagellates belonging to green algae *Chlamydomonas* (or *Volvocales*). *Chlamydomonas* is mostly generated in freshwater, but grown in seawater in some cases. The algae belonging to marine *Chlamydomonas* of the present invention indicate algae belonging to *Chlamydomonas*, which are generated in water or brackish water or can be grown in a culture medium containing sea salt.

*Chlamydomonas reinhardtii* is exemplified as the algae belonging to *Chlamydomonas*.

Examples of the algae belonging to *Chlorella* include *Chlorella vulgaris*, *Chlorella pyrenoidosa*, and *Chlorella sorokiniana*. Among these, *Chlorella sorokiniana* is preferable. *Chlorella sorokiniana* strain NIKE-2168 is exemplified as *Chlorella sorokiniana*.

Examples of the algae belonging to *Dunaliella* include *Dunaliella bioculata*, *Dunaliella salina*, and *Dunalliella tertiolecta*. *Dunaliella salina* NIES-2168 is exemplified as *Dunaliella salina*. *Dunaliella bioculata* NIES-2253 is exemplified as *Dunaliella bioculata*. *Dunaliella tertiolecta* NIES-2258 is exemplified as *Dunaliella tertiolecta*.

Examples of the algae belonging to *Nannochloropsis* include *Nannochloropsis oculata*. *Nannochloropsis oculata* NIES-2146 is exemplified as *Nannochloropsis oculata*.

In order to solve the above-described problem, the present inventors conducted search for algae which generate target oil/fat components with high efficiency and found that *Chlamydomonas* sp. JSC4 is particularly preferable.

[*Chlamydomonas* sp. JSC4]

Separation and purification of *Chlamydomonas* sp. JSC4 used in the present invention are performed by the following procedures.

That is, only one cell is isolated from brackish water samples collected from Taiwan Midwest coast and sterilized according to a conventional method. The sterilized cell is cultured under the light conditions of 20° C., 8 µmol photons/m$^2$/see to 15 µmol photons/m$^2$/sec for 12 hours of a light period and 12 hours of a dark period using an HSM agar culture medium showing the following compositions, the algae strain is established by performing subculture once every two weeks, the algae strain is identified as green algae belonging to *Chlamydomonas* through morphological observation and the like, and the algae strain is named strain JSC4.

TABLE 1

| Compositions | mg/L |
|---|---|
| $NH_4Cl$ | 500 |
| $MgSO_4 \cdot 7H_2O$ | 20 |
| $CaCl_2 \cdot 2H_2O$ | 10 |
| $K_2HPO_4$ | 1,440 |
| $KH_2PO_4$ | 720 |
| $Na_2EDTA$ | 50 |
| $ZnSO_4 \cdot 7H_2O$ | 22 |
| $H_3BO_3$ | 11.4 |
| $MnCl_2 \cdot 4H_2O$ | 5.1 |
| $CoCl_2 \cdot 6H_2O$ | 1.6 |
| $CuSO_4 \cdot 5H_2O$ | 1.6 |
| $(NH_4)6Mo_7O_{24} \cdot 4H_2O$ | 1.1 |
| $FeSO_4 \cdot 7H_2O$ | 5 |
| KOH | 16 |
| Agar | 15 g |
| pH (adjust by KOH) | 7.0 |

The algological properties of *Chlamydomonas* sp. JSC4 are as follows. FIG. 1 show a micrograph of vegetative cells (cells winch vigorously grow in a suitable growing environment and under the rich nutrient conditions) of *Chlamydomonas* sp. JSC4.

(Morphological Properties)

(1) The vegetative cell is oval and the size thereof is approximately 10 µm. The vegetative cell has two flagella having approximately the same size as the length of the cell. The vegetative cell has motility.

(2) The outer circumference of the vegetative cell is surrounded by a cell wall and one nucleus and one chloroplast are present in the inside thereof. In addition, mitochondria, a golgi body, a vacuole, and oil droplets are also recognized. The base of the chloroplast has a pyrenoid.

(Genital Form)

(1) Two to eight endospores are formed in a vegetative cell and equally distributed in the cell. The endospores have one nucleus and one chloroplast in the cell.

(2) Growth through binary division is carried out.

(Physiology or Biochemical Properties)

(1) Culture solution: *Chlamydomonas* sp. JSC4 can be generated in seawater or brackish water or can be grown in a culture solution containing sea salt.

(2) Photosynthesis performance: photoautotrophic growth using photosynthesis is possible.

(3) Dyes to be contained: chlorophyll a, chlorophyll b, and other carotenoids (4) Assimilation storage material: starch (5) Growth temperature range: 15° C. to 35° C. (optimum temperature of 25° C.)

(6) Growth pH range: pH 6.0 to 10.0 (optimum pH of 7.0)

In view of the description above, *Chlamydomonas* sp. JSC4 is identified as green algae belonging to *Chlamydomonas* from the morphological observation and the like.

The base sequence of 18S rDNA genes of *Chlamydomonas* sp. JSC4 is shown in SEQ ID NO; 1 of the sequence table. FIGS. 2 to 4 show comparison of 18S rDNA sequences of closely related *Chlamydomonas* species. The shading is a molecular marker sequence of *Chlamydomonas* sp. JSC4. The most closely related species of *Chlamydomonas* sp. JSC4 is *Chlamydomonas debaryana*, but *Chlamydomonas debaryana* is not the same species as *Chlamydomonas* sp. JSC4 when attention is paid to the molecular maker sequence. In this manner, *Chlamydomonas* sp. JSC4 is determined as a new microalgae strain in terms of comparison of 18S-rDNA sequences.

*Chlamydomonas* sp. JSC4 is internationally deposited as the receipt number FERM ABP-22266 under the provisions of the Budapest Treaty by National Institute of Technology and Evaluation (2-5-8 Kazusa-Kamatari, Kisarazu-shi, Chiba-ken) on Mar. 5, 2014.

[Culture Medium]

The culture medium used in the present invention is not limited as long as salt-tolerant algae are grown in the culture medium, but it is particularly preferable that the culture medium, containing sea salt contains seawater, concentrated seawater, or artificial seawater from a viewpoint of improving oil/fat producing ability.

For example, a modified Bold 3N medium can be particularly preferably used as such a culture medium.

Examples of the culture medium other than those described above include a modified Basal medium, a modified Bristol medium, a BG-11 medium, and a modified HSM, but a modified Bold 3N medium is particularly preferable from a viewpoint of capability of generating an oil/fat component with high efficiency.

The cultivation used in the present invention is carried out, for example, under the condition in which the content of nitrogen is low.

The cultivation under the condition in which the content of nitrogen is low may be cultivation in a nitrogen-deficient state due to nitrogen consumption accompanied by the growth or cultivation carried out by transplanting the alga body in a culture medium with a low nitrogen content.

In the present invention, the content of nitrogen to be contained in a culture medium can be evaluated by measuring the content of nitrate contained in the culture medium at a wavelength of 220 nm.

The evaluation method is not limited thereto. The content of nitrogen contained in a culture medium can also be evaluated by measuring the content of nitrate or ammonium salts using an ion sensor or through absorbance measurement using a coloring reagent.

The measurement method is carried out by the method reported by Collos et al. in 1999 (Reference: Journal of Applied Phycology, Volume 11, pp. 179 to 184 (1999)).

A specific measurement method will be described in examples below.

The compositions of the modified Bold 3N medium used in the present invention are shown below.

TABLE 2

| Compositions |
|---|
| $NaNO_3$ |
| $K_2HPO_4$ |
| $MgSO_4 \cdot 7H_2O$ |
| $KH_2PO_4$ |
| NaCl |
| $CaCl_2 \cdot 2H_2O$ |
| $FeCl_3 \cdot 6H_2O$ |
| $Na_2 \cdot EDTA \cdot 2H_2O$ |
| $ZnSO_4 \cdot 7H_2O$ |
| $CoSO_4 \cdot 7H_2O$ |
| $MnSO_4 \cdot 5H_2O$ |
| $Na_2MoO_4 \cdot 2H_2O$ |
| $Na_2SeO_3$ |
| $NiCl_2 \cdot 6H_2O$ |
| Sea Salt |

(Sea Salt)

In the present invention, it is found that the culture method that increases the concentration of salts (the mass % of the sea salt in the entire culture medium) in a culture medium in a stepwise manner greatly affects the oil/fat component producing ability. Accordingly, for example, the production efficiency of oil/fat components can be improved by adding sea salt at a predetermined concentration to the above-described culture medium in a stepwise manner.

Conventionally known sea salt can be exemplified as the sea salt used in the present invention. The sea salt used in the present invention may be obtained by evaporating, drying, and solidifying seawater or by using seawater or a concentrated solution of seawater, but it is more preferable to use sea salt which is the solid content of seawater in order to adjust the concentration of sea salt to be contained in a culture medium.

Moreover, artificial seawater can be used. The artificial seawater used in the present invention is powder or a concentrated solution winch is artificially adjusted by imitating the compositions of seawater. The artificial seawater may be replaced by natural seawater because of availability, reproducibility, and the low cost, at the time of breeding or culturing organisms for which seawater is required. Commercially available artificial seawater can be used and may become a component close to seawater by being diluted with tap water or distilled water depending on the application because the commercially available artificial seawater contains sodium chloride as a main component and various inorganic salts, a pH adjusting agent, or the like.

Further, it is possible to adjust and use salts, other than the above-described sea salt, which can be used as a culture medium suitable for the purpose of the present invention.

(Stepwise Control of Salt Concentration)

In the present invention, it is found that stepwise control of the salt concentration greatly affects the oil/fat production efficiency.

As described in examples below, the growth of algae is inhibited when the algae are cultured at a high salt concentration, but it is obvious that the lipid content is increased. Therefore, for the purpose of increasing the amount of lipids to be produced, it is preferable that algae are cultured at a low salt concentration such that the cells are increased so as to have a predetermined number, the concentration of salts in a culture medium is increased, algae are cultured at a high salt concentration, and then the content of lipids in the cells are increased.

In the present invention, the concentration of salts in a culture medium at the time of starting cultivation of salt-tolerant algae indicates "the salt concentration in the first stage." In a case where the concentration of salts in a culture medium is increased only once, the concentration of salts in a culture medium during the harvest becomes "the salt concentration in the second stage." In a case where the cultivation is performed by increasing the salt concentration in multiple stages, for example, the concentration of salts in a culture medium is increased N−1 times (N represents an integer of 3 or greater), the concentration of salts in a culture medium during the harvest becomes "the salt concentration in the N-th stage."

From a viewpoint of increasing the growth efficiency of algae, the concentration of salts in a culture medium in the first stage is preferably in the range of 0.5% by mass to 5% by mass, more preferably in the range of 0.5% by mass to 3% by mass, and still more preferably in the range of 0.5% by mass to 2% by mass.

Although the culture period in the first stage varies depending on the growth rate of salt-tolerant algae to be used, the period is preferably in the range of 1 day to 3 days.

As described above, it is preferable that algae are cultured under the condition in which the nitrogen content is low in order to increase the lipid content.

The cultivation under the condition in which the nitrogen content is low may be cultivation in a nitrogen-deficient state due to nitrogen consumption accompanied by the growth or cultivation carried out by transplanting the alga body in a culture medium with a low nitrogen content. From a viewpoint that the growth of algae is inhibited when the algae are cultured under the condition in which the nitrogen content is low, for the purpose of increasing the amount of lipid to be produced, it is preferable that algae are cultured under the condition in which the nitrogen content is sufficient such that the cells are increased to have a predetermined number, and then the algae are cultured under the condition in which the nitrogen content is low such that the content of lipids in the cells is increased.

The lipid production efficiency can be increased by controlling the nitrate content in addition to the control of the salt concentration. From such a viewpoint, when the content of nitrate in the culture medium at a wavelength of 220 nm is measured, it is preferable that the salt concentration in the second stage is increased when the content of nitrate becomes 10 mg/L or less.

In the method for producing an oil/fat component of the present invention, it is preferable that salt-tolerant algae are cultured in a culture medium of which the salt concentration is increased by 0.5% to 5% in a stepwise manner.

Examples of the method for controlling the salt concentration in a stepwise manner include a "two-stage culture method" that increases the concentration of salts in a culture medium only once and a "multi-stage culture method (also referred to as a gradient method)" that increases the concentration of salts in a culture medium N−1 times (N represents an integer of 3 or greater). Further, in the present invention, the culture method in which the salt concentration is constant is referred to as a batch method.

(Two-Stage Culture Method)

In the two-stage culture method, the salt concentration to be increased is preferably in the range of 0.5% to 5% and more preferably in the range of 1% to 5%. Although the culture period in the second stage varies depending on the growth rate of salt-tolerant algae to be used, the period is preferably in the range of 3 days to 8 days.

(Multi-Stage Culture Method)

In the multi-stage culture method, the salt concentration to be increased for each stage is preferably in the range of 0.5% to 2% and more preferably in the range of 0.5% to 1.5%. Although the salt concentration to be increased for each stage may vary, it is preferable that the salt concentration to be increased for each stage is the same from the viewpoint of ease of cultivation. Similarly, the culture period in each stage may vary, but it is preferable that the culture periods are the same as each other. The cultivation period in each stage is preferably in the range of 1 day to 3 days and more preferably 1 day.

The number of stages (N described above) is preferably in the range of 3 to 8 and more preferably in the range of 4 to 6. Although the phase culture period in the second stage to the N-th stage varies depending on the growth rate of salt-tolerant algae to be used, the period thereof is preferably in the range of 3 days to 8 days and more preferably in the range of 4 days to 6 days.

In addition, in a case where mass culture of algae is assumed, seawater is conveniently used, but sodium chloride can be preferably used because sodium chloride has the same effects as those of seawater with respect to generation of oils and fats.

(Culture Method)

In the present invention, salt-tolerant algae can be cultured according to a conventionally known method.

In the present invention, the above-described culture medium can be used for the cultivation.

A stationary culture method can be used as the culture method used in the present invention, but a shaking culture method or a deep aeration stirring culture method is preferable as the culture method when alga body productivity of algae or oil/fat component productivity is considered. The shaking culture may be reciprocal shaking or rotary shaking. The alga body can be generated typically at a culture temperature of 15° C. to 40° C.

As described above, when the salt-tolerant algae are cultured according to the above-described culture method, algae can be stably grown and salt-tolerant algae with a high ratio of oil/fat components can be obtained.

Further, the light condition is not particularly limited as long as photosynthesis can be carried out, but continuous light is preferable.

After the cultivation, the recovery of the alga body from a culture solution used as a method for obtaining crude oils and fats can be performed according to a centrifugal separation method, which is a typical method, or a filtration method using filter paper or a glass filter. The alga body recovered in this manner may be used as it is or can be made into a dry alga body according to a freeze-drying method or a hot air drying method. Oil/fat components can be extracted from the obtained alga body or dry alga body.

In the present invention, it is preferable that the above-described method, is performed by typically supplying carbon dioxide.

A conventionally known method can be used as the method for supplying carbon dioxide. For example, supply of carbon dioxide can be suitably performed by aerating a culture solution.

The oil/fat component generated in the present invention is triacylglyceride.

Triacylglyceride is expected to be used as a bio-diesel fuel through alkyl esterification.

An ester of glycerin and a fatty acid is used as a compound exemplified as triacylglyceride in the present invention and a higher saturated or unsaturated fatty acid having 10 to 30 carbon atoms is used as a fatty acid.

Moreover, the present invention is to provide a method for producing a higher unsaturated fatty acid useful as a bio-diesel fuel.

That is, a higher unsaturated fatty acid with high combustion efficiency can be produced by hydrolyzing the oil/fat component obtained in the method of the present invention.

Examples of the higher unsaturated fatty acid with high combustion efficiency include oleic acid and linoleic acid. Between them, oleic acid is particularly preferable from a viewpoint of particularly high combustion efficiency.

As a result of examination of the optimum concentration of sea salt for generating the above-described higher unsaturated fatty acid, the concentration thereof is preferably in the range of 0.5% by mass to 5% by mass and particularly preferably in the range of 2.0% by mass to 5% by mass.

(Method for Extracting Oils and Fats)

A typical method for extracting oils and fats can be used as the method for extracting an oil/fat component from an alga body. Particularly, a typical extraction method using an organic solvent such as a chloroform- or methanol-based solvent, which is typified by a Folch method or a Bligh-Dyer method, can be used, but the extraction method is not limited thereto.

EXAMPLES

The present invention will be described more in detail with reference to examples below, but the present invention is not limited to the examples.

(Measurement of Algae Concentration in Culture Solution)

A liquid sample from a photobioreactor was filtered using a filter having a pore diameter of 0.45 μm, which was precisely weighed in advance, freeze-dried until the weight of the filtered sample became constant, and then precisely weighed. A difference in filter mass before and after the filtration was divided by the amount of the filtered liquid sample, and then the algae concentration was determined.

(Measurement of Nitrogen Content in Culture Solution)

A liquid sample from a photobioreactor was filtered using a filter having a pore diameter of 0.22 μm, and diluted in 20 times with distilled water. The nitrate concentration was determined by the optical concentration at a wavelength of 220 nm ($OD_{220}$) using a UV/VIS spectrophotometer.

Figures 5, 6:
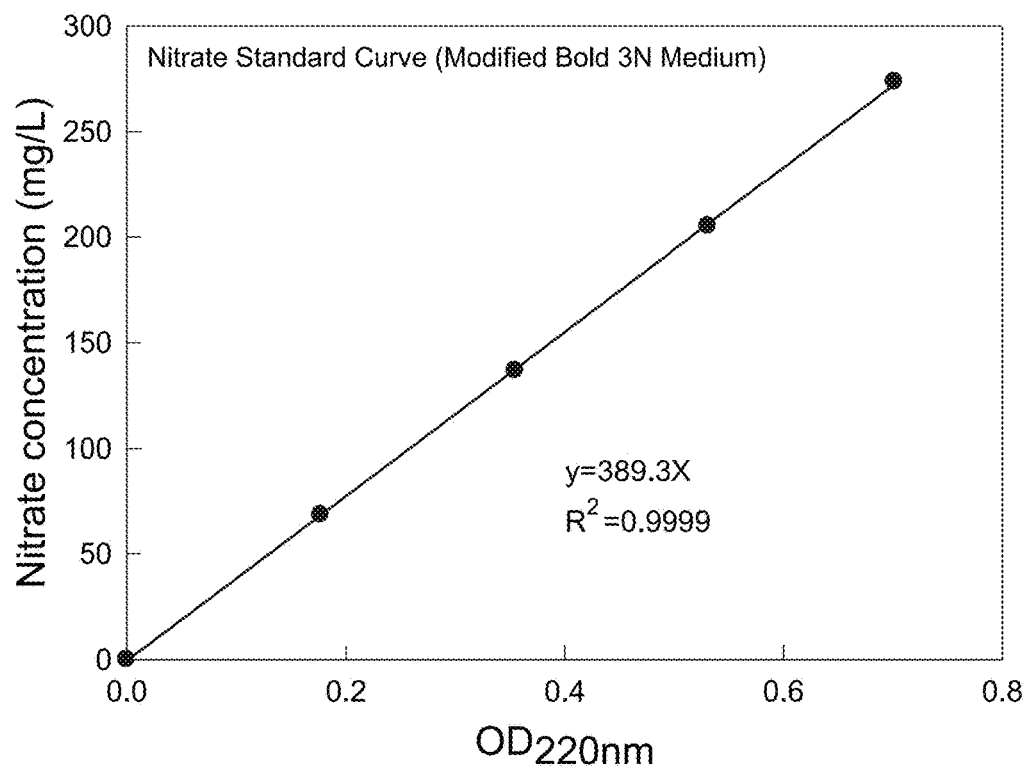
FIG. 5 is a calibration curve showing the relation between $OD_{220\,nm}$ and the nitrate concentration.
FIG. 6 shows results of analyzing compositions of fatty acids of *Chlamydomonas* sp. JSC4 cultured under the nitrogen-rich conditions and the nitrogen-deficient conditions.
Figure 7:
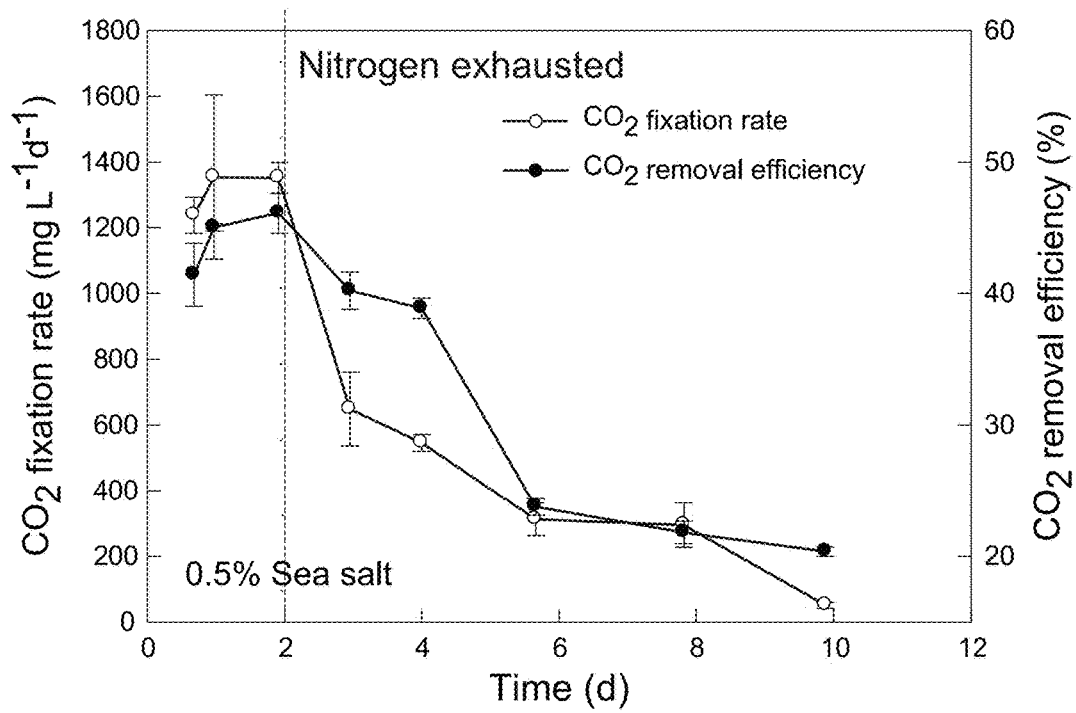
FIG. 7 shows results of analyzing $CO_2$ fixation ability of *Chlamydomonas* sp. JSC4 cultured at different seawater concentrations.
Figure 8:
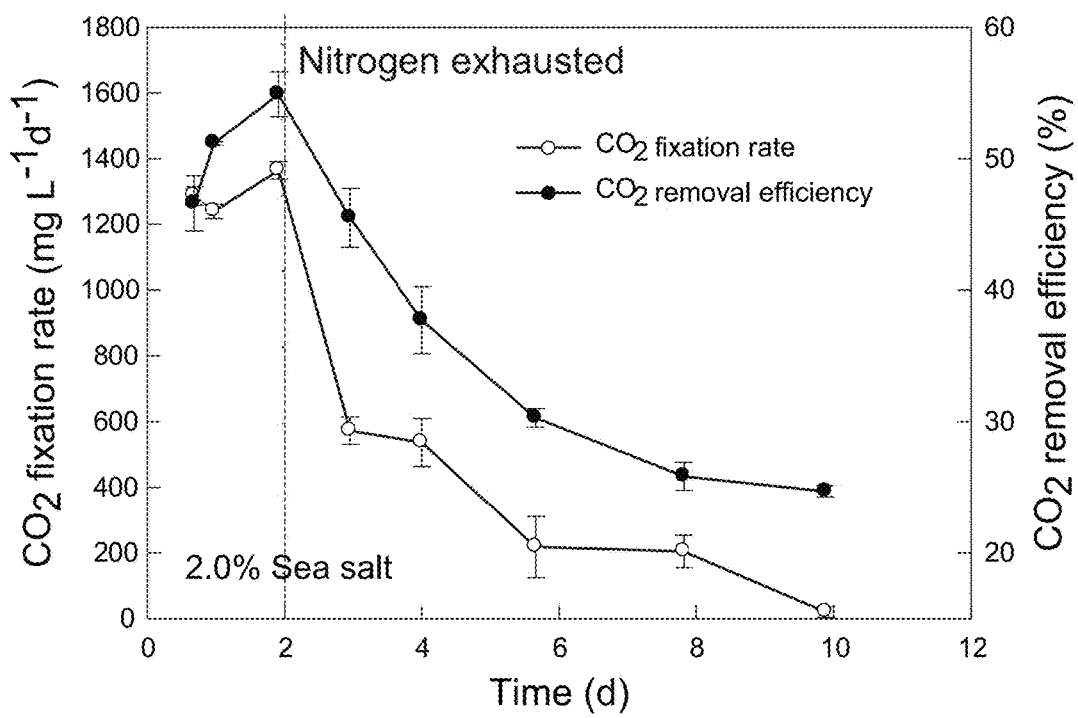
FIG. 8 shows results of analyzing $CO_2$ fixation ability of *Chlamydomonas* sp. JSC4 cultured at different seawater concentrations.
Figure 9:
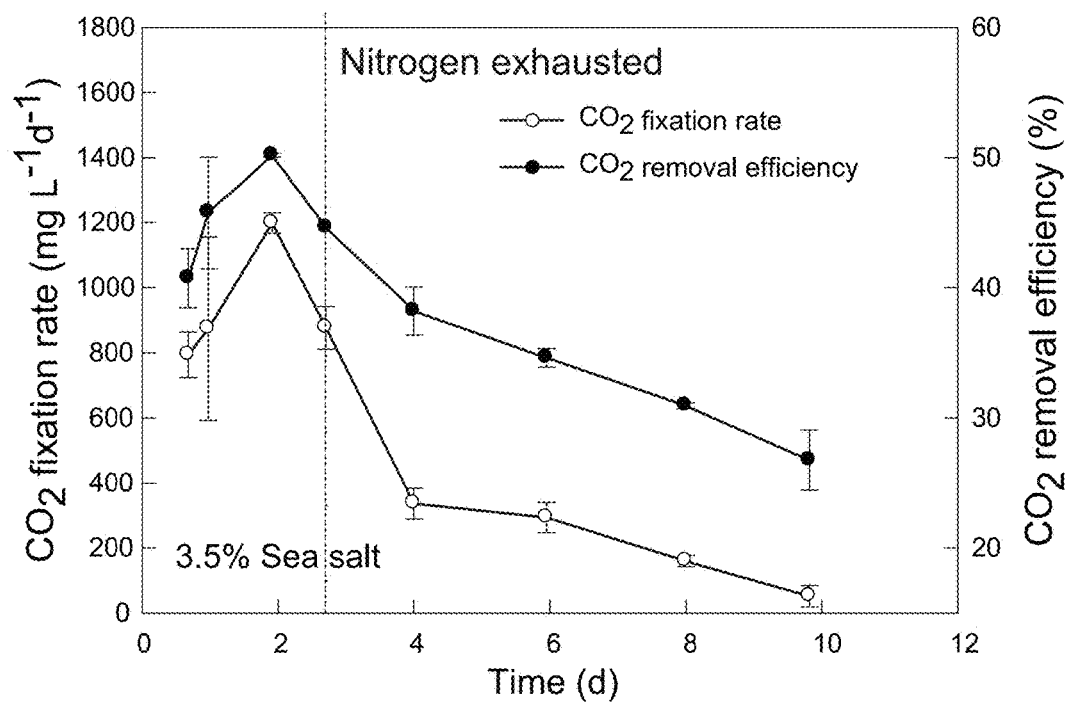
FIG. 9 shows results of analyzing $CO_2$ fixation ability of *Chlamydomonas* sp. JSC4 cultured at different seawater concentrations.
Figure 10:
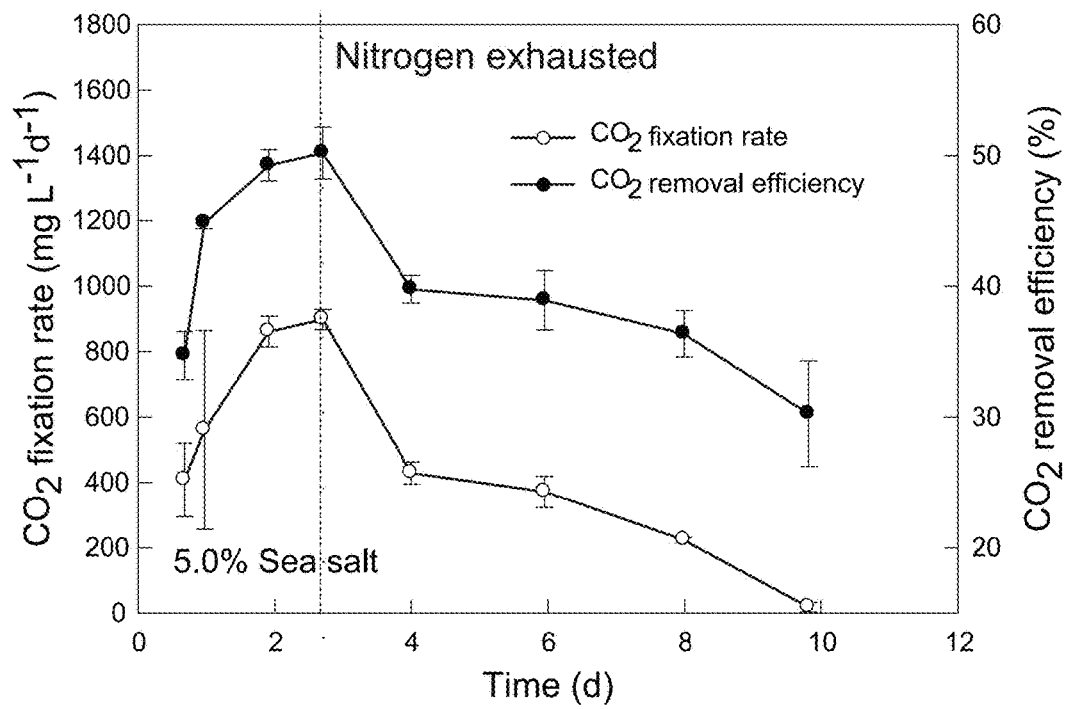
FIG. 10 shows results of analyzing $CO_2$ fixation ability of *Chlamydomonas* sp. JSC4 cultured at different seawater concentrations.
Figure 11:
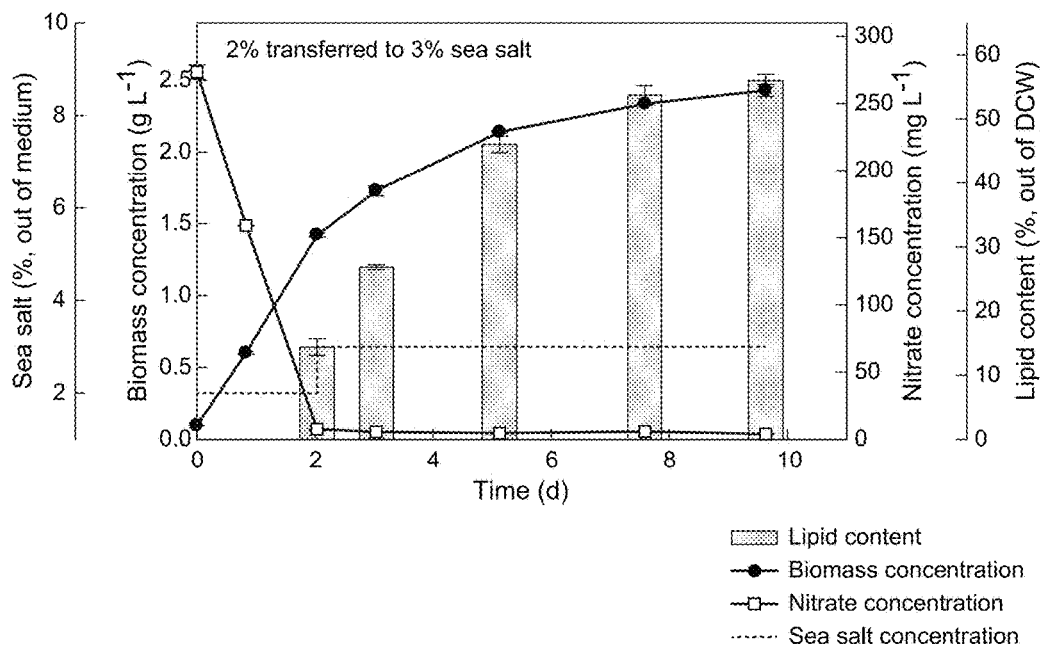
FIG. 11 shows results of time course profiles of the biomass concentration and the lipid content obtained by culturing *Chlamydomonas* sp. JSC4 according to a two-stage culture method.
Figure 12:
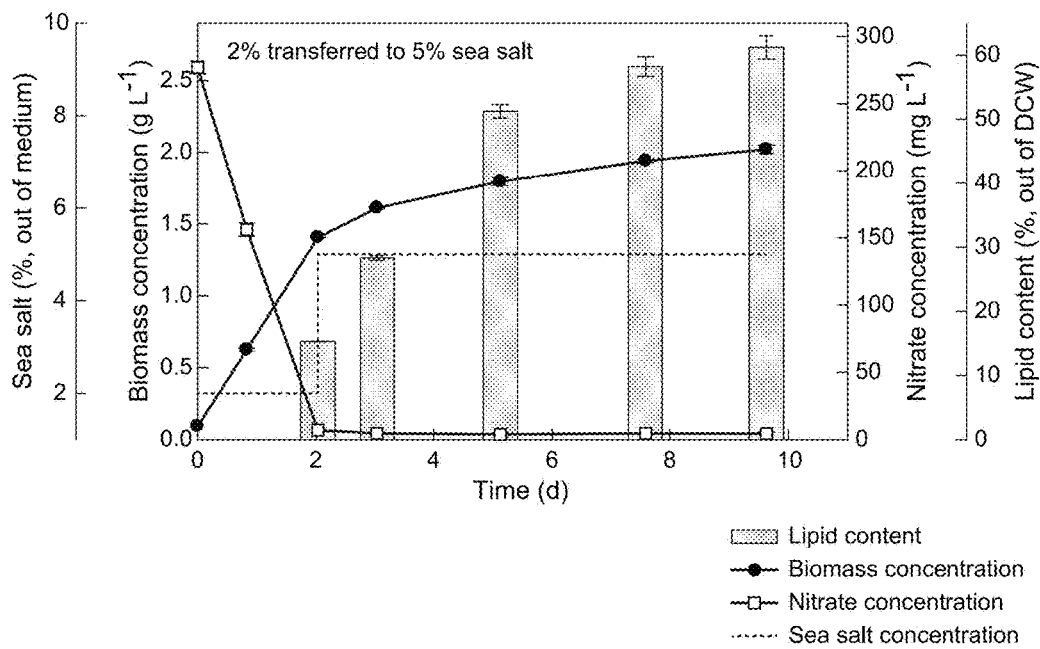
FIG. 12 shows results of time course profiles of the biomass concentration and the lipid content obtained by culturing *Chlamydomonas* sp. JSC4 according to the two-stage culture method.
Figure 13:
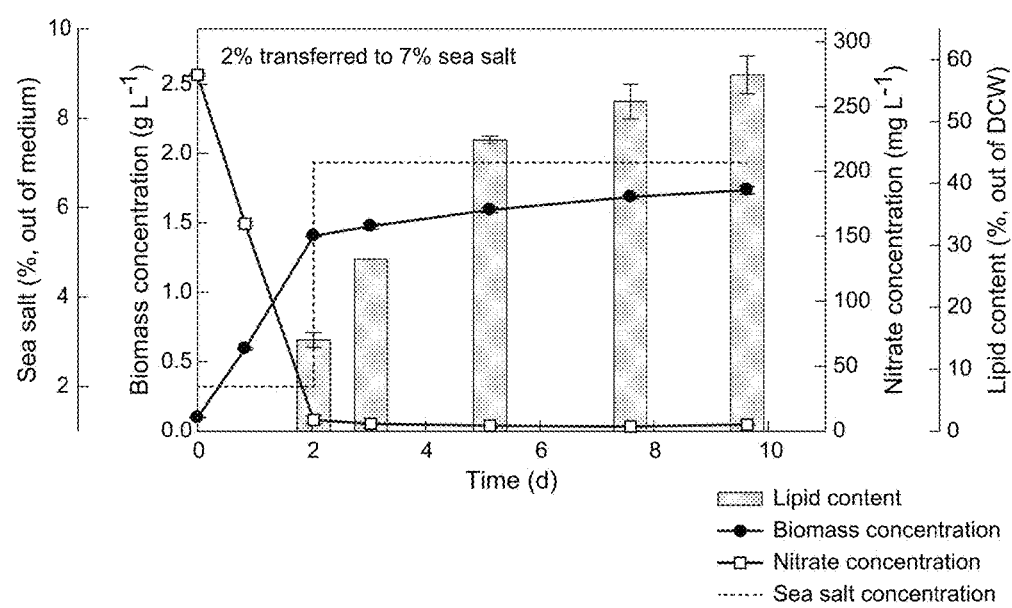
FIG. 13 shows results of time course profiles of the biomass concentration and the lipid content obtained by culturing *Chlamydomonas* sp. JSC4 according to the two-stage culture method.
Figure 15:
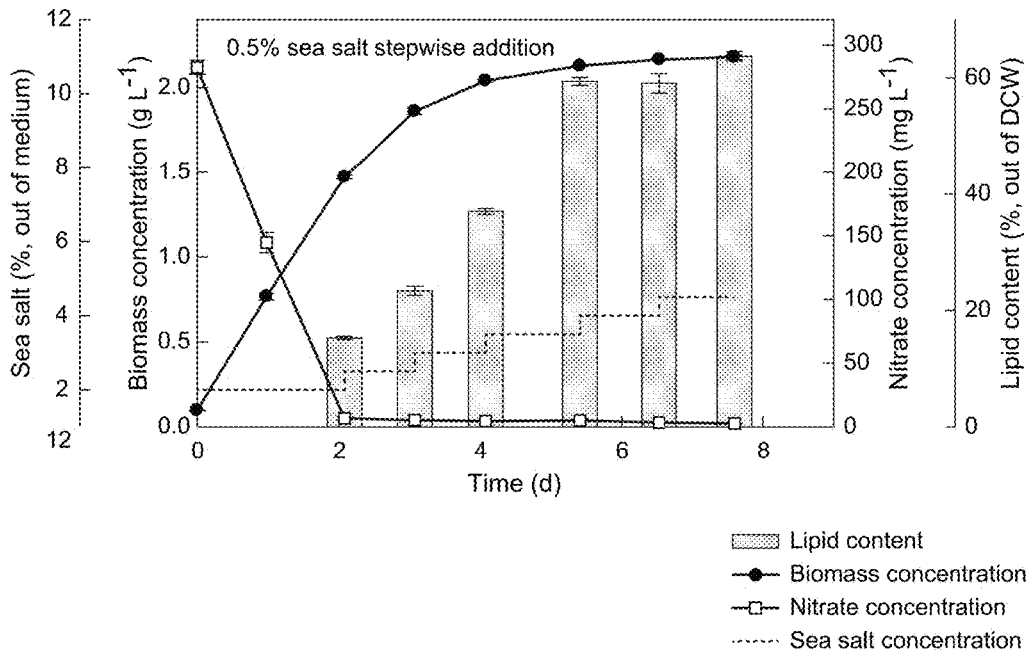
FIG. 15 shows results of time course profiles of the biomass concentration and the lipid content obtained by culturing *Chlamydomonas* sp. JSC4 according to a gradient method.
Figure 16:
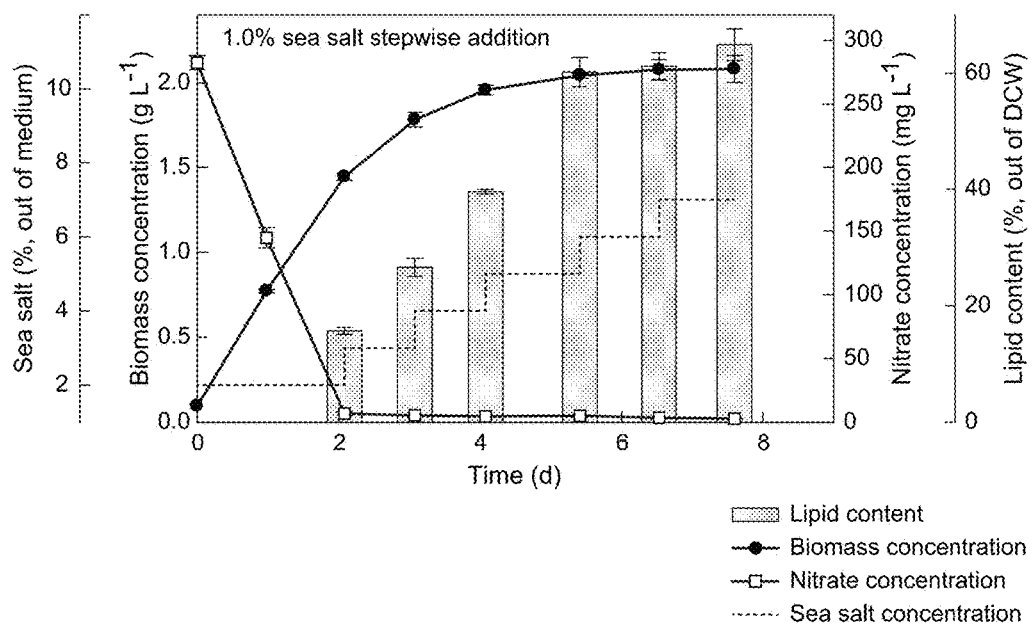
FIG. 16 shows results of time course profiles of the biomass concentration and the lipid content obtained by culturing *Chlamydomonas* sp. JSC4 according to the gradient method.
Figure 17:
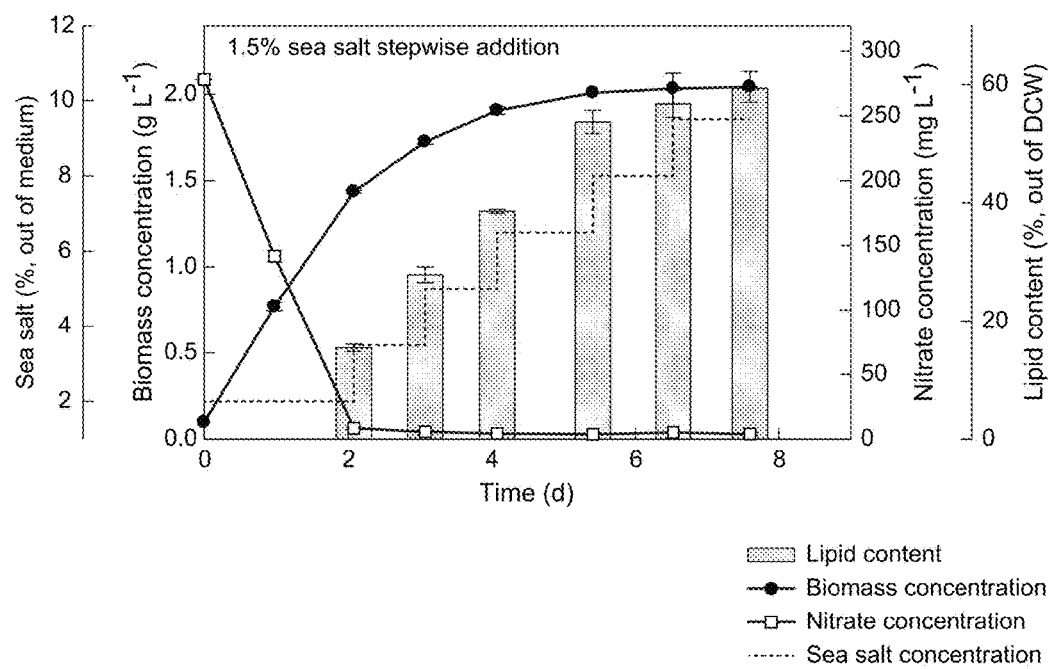
FIG. 17 shows results of time course profiles of the biomass concentration and the lipid content obtained by culturing *Chlamydomonas* sp. JSC4 according to the gradient method.

That is, the value at $OD_{220}$ was converted to the nitrate concentration using the calibration curve consisting of the relation between $OD_{220}$ and the nitrate content shown in FIG. 5.

(Analysis of Oil/Fat Component in Alga Body)

15 mg of a freeze-dried alga body was put into a micro vial in which 0.5 g of a glass bead having a diameter of 0.5 mm was present, a 1 mL KOH solution having a concentration of 0.5 M was added thereto, and a crushing treatment was carried out using a bead beater homogenizer for 40 minutes. The treatment liquid was transferred to a 50 mL capacity heat-resistant glass bottle while being prewashed with a 7 mL KOH solution having a concentration of 0.5 M, and the bottle was tightly sealed, and then the treatment liquid was treated in a water bath at a temperature of 100° C. for 15 minutes. The resultant was cooled to room temperature, a 8 mL HCl methanol solution having a concentration of 0.7 M and 10 mL of a 14% (v/v) boron trifluoride methanol solution (manufactured by Sigma-Aldrich Co. LCC.) were added thereto, and the solution was treated in the water bath again at 100° C. for 15 minutes. After the solution was cooled to room temperature, 4 mL of a saturated salt solution and 3 mL of n-hexane were added thereto, and the solution was stirred by a vortex mixer for 5 minutes. The stirred solution was transferred to a 50 mL capacity plastic centrifuge tube and centrifuged at 7,000 rpm for 2 minutes. 100 µL of a supernatant was put into an Eppendorf tube, 890 µL of n-hexane and 10 µL of an internal standard substance (methyl pentadecanic acid, Sigma-Aldrich Co. LCC.) were added thereto, and the supernatant was centrifuged at 10,000 rpm for 3 minutes and then analyzed by a GCMS analyzer.

A DB-23 capillary column (0.25 mmφ×60 m, film thickness of 0.15 µm, Agilent Technologies, Japan, Ltd.) was installed on the GCMS analyzer (GCMS-QP2010 Plus, Shimadzu Corporation) and 2.3 mL of helium gas was allowed to flow therein every minute. The temperatures of an injector, ion source, and interface were respectively set as 230° C., 230° C., and 250° C. Further, the column temperature was held at 50° C. for 1 minute after sample injection, increased to 175° C. by being increased 25° C. every minute, further increased to 230° C. by being increased 4° C. every minute, and then held for 5 minutes. 1 µL of the above-described supernatant was injected into the column, the column was separated at a split ratio of 5:1, each component of fatty acid methyl ester was detected in a full-scan mode of 50 m/z to 500 m/z and quantified based on the additive amount of the internal standard, and then the quantified result was set as the amount of oils and fats.

(Analysis of $CO_2$ Fixation Ability)

The growth rate with respect to the time plot based on the weight of a dry alga body was calculated using a time course profile of the biomass concentration (g/L).

The biomass production rate ($P_{biomass}$; mg/L/d) can be acquired by the following equation.

$$P_{biomass} = \Delta X / \Delta t$$

In the equation, $\Delta X$ represents the amount of change in the biomass concentration (mg/L) in the culture time $\Delta t(d)$.

Further, the $CO_2$ fixation rate ($P_{CO2}$; mg/L/d) can be acquired by the following equation.

$$P_{CO2} \text{ (mg/L/d)} = 1.88 \times P_{biomass}$$

As a typical molecular formula of the biomass of algae, $CO_{0.48}H_{1.83}N_{0.11}P_{0.01}$ was used.

The $CO_2$ fixation rate (%) can be acquired by the following equation.

$$CO_2 \text{ fixation rate (\%)} = 100 \times (C_{CO2,influent} - C_{CO2,effluent}) / C_{CO2,influent}$$

In the equation, $C_{CO2,influent}$ and $C_{CO2,effluent}$ respectively represent the influent concentration and the effluent concentration of $CO_2$.

Reference Example 1

(Comparison of Culture Medium)

Respectively 1 L of the modified Basal medium, modified Bristol medium, BG-11 medium, modified Bold 3N medium, and modified High Salt Medium (HSM) whose compositions were listed in Table 3 were prepared, added to photobioreactors having a capacity of 1 L, and autoclave-sterilized. *Chlamydomonas* sp. JSC4 was cultured for 5.7 days under the conditions in which *Chlamydomonas* sp. JSC4 was inoculated to the respective photobioreactors such that the algae concentration became approximately 100 mg/L, the photobioreactors were continuously irradiated with fluorescent light having an intensity of 200 µmol photons/m²/sec at room temperature for 24 hours, 50 mL of 2% carbon dioxide-containing air was aerated every minute, and the photobioreactors were stirred using a stirrer at 200 rpm.

The analysis results of oil/fat components of each culture solution are listed in Table 4. The oil/fat content in an alga body and the lipid productivity per culture solution of the modified Bold 3N medium were the highest.

TABLE 3

| Culture medium (mg L⁻¹) | Modified Basal | Modified Bristol | BG-11 | Modified Bold 3N | Modified HSM |
|---|---|---|---|---|---|
| NaNO₃ | | 375 | 375 | 375 | |
| KNO₃ | 420 | | | | |
| NH₄Cl | | | | | 250 |
| K₂HPO₄ | 1440 | 75 | 30 | 38.3 | 1440 |
| MgSO4•7H₂0 | 1000 | 75 | 75 | 75 | 20 |
| KH₂PO₄ | | 175 | | 88 | 740 |
| NaCl | | 25 | | 25 | |
| Citric acid anhydrous | | | 6 | | |
| Na₂CO₃ | | | 20 | | |
| CaCl₂•2H₂0 | 110.6 | 25 | 36 | 25 | 10 |
| FeCl₃•6H₂0 | | 5 | | 1.77 | 0.15978 |
| FeSO₄•7H₂0 | 49.8 | | | | |
| Ferric ammonium citrate | | | 6 | | |
| Na₂•EDTA•2H₂0 | 500 | | 1 | 5.53 | 0.3 |
| ZnSO₄•7H₂0 | 88.2 | 0.287 | 0.222 | 0.073 | |
| ZnCl₂ | | | | | 0.00328 |
| CoSO₄•7H₂0 | | | | 0.016 | |

TABLE 3-continued

| Culture medium (mg L$^{-1}$) | Modified Basal | Modified Bristol | BG-11 | Modified Bold 3N | Modified HSM |
|---|---|---|---|---|---|
| Co(NO$_3$)$_2$•6H$_2$O | 4.9 | | 0.0049 | | |
| CoCl$_2$•6H$_2$O | | | | | 0.0026 |
| MnSO$_4$•5H$_2$O | | 0.169 | | 0.584 | |
| MnCl$_2$•4H$_2$O | 14.4 | | 1.81 | | 0.415 |
| Na$_2$MoO$_4$•2H$_2$O | 11.9 | | 0.39 | 0.00148 | 0.00726 |
| (NH$_4$)$_6$Mo$_7$O$_{24}$•4H$_2$O | | 0.00124 | | | |
| Na$_2$SeO$_3$ | | | | 0.00173 | |
| NiCl$_2$•6H$_2$O | | | | 0.00149 | |
| H$_3$BO$_3$ | 114.2 | 0.061 | 2.86 | | 0.1855 |
| CuSO$_4$•5H$_2$O | 15.7 | 0.0025 | 0.0079 | | |
| CuCl$_2$•2H$_2$O | | | | | 0.000012 |
| Sea Salt | 20 g | 20 g | 20 g | 20 g | 20 g |

TABLE 4

| Culture medium | Modified Basal | Modified Bristol | BG-11 | Modified Bold 3N | Modified HSM |
|---|---|---|---|---|---|
| Oil/fat content in alga body (%) | 24.1 | 35.7 | 36.0 | 41.1 | 34.8 |
| Lipid productivity per culture solution (mg/L/d) | 90.3 | 125.6 | 148.4 | 155.0 | 123.8 |

Reference Example 2

(Effects of Addition of Sea Salt (Batch Method))

Respectively 1 L of culture medium in which the amounts of sea salt to be added to the modified Bold 3N medium whose compositions were listed in Table 3 were set as 0.5%, 2%, 3.5%, and 5% (w/v) were prepared, added to photobioreactors having a capacity of 1 L, and autoclave-sterilized. *Chlamydomonas* sp. JSC4 was cultured for 10 days under the conditions in which *Chlamydomonas* sp. JSC4 was inoculated to the photobioreactors such that the algae concentration became approximately 100 mg/L, the photobioreactors were continuously irradiated with fluorescent light having an intensity of 200 μmol photons/m$^2$/sec at room temperature for 24 hours, 50 mL of 2% carbon dioxide-containing air was aerated every minute, and the photobioreactors were stirred using a stirrer at 200 rpm. In the present invention, the culture method in which the salt concentration is constant is referred to as the batch method.

In all cases, the content of nitrate in a culture solution was low along with the growth of an alga body and the content thereof became 10 mg/L or less for 1.9 days or 2.7 days. Next, the lipid content in an alga body and the lipid productivity were significantly increased. Particularly in a case where 2%, 3.5%, and 5% of sea salt were added, the contents of oils and fats in an alga body reached a high value of 50% or greater and the maximum lipid productivity was 140 mg/L/d or greater, which was extremely high.

TABLE 5

| Amount of Sea Salt to be added | 0.5% | 2% | 3.5% | 5% |
|---|---|---|---|---|
| Culture day on which content of nitrate in culture solution became 10 mg/L or less | 1.9 days | 1.9 days | 2.7 days | 2.7 days |
| Lipid content in alga body at which content of nitrate in culture solution became 10 mg/L or less (%) | 15.6 | 15.8 | 15.3 | 14.5 |

TABLE 5-continued

| Amount of Sea Salt to be added | 0.5% | 2% | 3.5% | 5% |
|---|---|---|---|---|
| Lipid productivity per culture solution at which content of nitrate in culture solution became 10 mg/L or less (mg/L/d) | 108.9 | 110.7 | 78.9 | 55.9 |
| Culture day on which lipid productivity per culture solution became maximum | 5.7 days | 5.7 days | 6.0 days | 6.0 days |
| Lipid productivity per culture solution during 3 days from which content of nitrate in culture solution became 10 mg/L or less (mg/L/d) | 116.3 | 158.9 | 142.6 | 148.7 |
| Lipid content in alga body on tenth day of cultivation | 38.7 | 53.5 | 55.1 | 64.0 |

Reference Example 3

(Effects of Cultivation Under Nitrogen-Deficient Condition on Quality of Biodiesel)

The quality of biodiesel is evaluated by the ratio of unsaturated fatty acids to saturated fatty acids. The content of the saturated fatty acids in biodiesel affects oxidation suppression at a high temperature. Meanwhile, the amount of the unsaturated fatty acids affects the fluidity at a low temperature. The amount of the saturated fatty acids in the biodiesel being the same as the amount of the unsaturated fatty acids in the biodiesel is important for the purpose of providing excellent characteristics at a low temperature and a high temperature for the biodiesel. The profile of fatty acids affects environmental stress caused by the nutrients in a culture medium, the outside temperature, and the light intensity. Among these, the nitrogen-deficient condition is the most important factor that affects the fat metabolism of algae.

FIG. 6 shows the compositions of fatty acids of *Chlamydomonas* sp. JSC4 cultured under the nitrogen-rich conditions and the nitrogen-deficient conditions. In FIG. 6, as a control, the compositions of fatty acids are compared to the compositions of fatty acids derived from soybean oil. The culture conditions of *Chlamydomonas* sp. JSC4 are the same as those in Reference Example 2.

As shown in FIG. 6, in regard to accumulation of oils and fats in *Chlamydomonas* sp. JSC4 under the nitrogen-deficient conditions, it was confirmed that oleic acid (C18:1) was likely to be increased and linolenic acid (C18:3) was likely to be decreased. According to the characteristics of biodiesel, when oleic acid is contained at a high ratio, biodiesel has more excellent oxidation stability and suitable clogging points (CFPP) at a low outside temperature. Moreover, the upper limit of the content of linolenic acid (C18:3) is set to 12% (m/m) based on the European biofuel standard (EN14214). Accordingly, it was confirmed that oils and fats produced by *Chlamydomonas* sp. JSC4 has the quality suitable for producing biofuels.

Further, as shown in FIG. 6, compared to the compositions of fatty acids derived from soybean oil, the content of saturated fatty acids was high and the content of polyvalent unsaturated fatty acids (n≥2) was low in *Chlamydomonas* sp. JSC4. Typically, the high content of saturated fatty acids in oils and fats leads to excellent fluidity and density for biofuels. Meanwhile, the low content of polyvalent unsaturated fatty acids leads to improvement of oxidation stability at a low outside temperature and provision of suitable clogging points. Therefore, from the viewpoint that *Chlamydomonas* sp. JSC4 has a profile of fatty acids suitable for oils and fats, it was confirmed that *Chlamydomonas* sp. JSC4 is a strain suitable for production of biofuels.

Reference Example 4

(Effects of Controlling Sea Salt and Nitrogen Source on $CO_2$ Fixation of *Chlamydomonas* sp. JSC4)

The $CO_2$ fixation ability of *Chlamydomonas* sp. JSC4 that was cultured at culture media whose contents of sea salt were different from each other was examined at constant time intervals. The results thereof are shown in FIGS. 7 to 10. As shown in FIGS. 7 to 10, the $CO_2$ fixation rate and the $CO_2$ fixed-speed, at different concentrations of sea salt show the same tendency over the elapsed time. In other words, gradually decreasing bell type curves were shown after reaching the maximum values from 2 to 3 days of cultivation.

In FIGS. 7 to 10, the maximum values of the $CO_2$ fixation rate and the $CO_2$ fixed-speed were obtained under the condition in which the amount of sea salt to be added was 2% and the values were respectively 54.9% and 1319.0 mg/L/d. From this excellent $CO_2$ fixation ability, it was confirmed that *Chlamydomonas* sp. JSC4 is a strain which can be practically applied to $CO_2$ fixation using industrial gas.

Example 1

(Examination of Two-Stage Culture Method for Promoting Lipid Accumulation of *Chlamydomonas* sp. JSC4)

In order to improve the content of lipids in an alga body and the lipid productivity, the two-stage culture method was attempted. First, the cultivation in the first stage was performed for approximately 2 days using the modified Bold 3N medium containing 2% of sea salt. Next, after at least 95% of the nitrogen sources were depleted, culture media were replaced with nitrogen source-limiting media containing 3% of sea salt, 5% of sea salt, and 7% of sea salt, and cultivation in the second stage was performed.

As shown in FIGS. 11 to 14, the lipid contents of *Chlamydomonas* sp. JSC4 on which cultivation in the second stage was performed for 7 days from the day when the culture media were replaced with the nitrogen source-limiting media containing 3% of sea salt, 5% of sea salt, and 7% of sea salt were respectively 56%, 61%, and 58%. These lipid contents were approximately four times the lipid content which was approximately 15% obtained after the cultivation in the first stage. When the cultivation in the second stage was performed using the 5% sea salt-containing culture medium for 7 days, the lipid content was significantly increased along with the increase in the sea salt concentration and the lipid content was 61.2%. Further, when the cultivation in the second stage was performed using the 3% sea salt-containing culture medium for 3 days, the lipid productivity was 183.9 mg/L/d.

It was confirmed that the two-stage culture method significantly promoted the lipid content of the *Chlamydomonas* sp. JSC4 and this lipid content was higher than the lipid content obtained by the batch method.

Example 2

(Examination of Effects of Cell Growth and Lipid Accumulation in *Chlamydomonas* sp. JSC4 Cultured in Culture Medium to Which Sea Salt was Added in Multiple Stages)

The cultivation of *Chlamydomonas* sp. JSC4 using a high-concentration sea salt-containing culture medium promotes the lipid content, but may cause a decrease in the growth rate. In order to achieve high lipid productivity, it is preferable to reduce growth inhibition due to the stress of the salt concentration. For this reason, the gradient method was attempted.

First, the cultivation was performed for approximately 2 days using the modified Bold 3N medium containing 2% of sea salt. Next, after at least 95% of the nitrogen sources were depleted, the cultivation was performed for 5 days under the condition in which the concentration of salts in the culture solution was allowed to be increased by 0.5%, 1.0%, and 1.5% per day in a stepwise manner. The results thereof are shown in FIGS. 15 to 18.

As shown in FIGS. 15 to 18, it was confirmed that the lipid content was rapidly increased without the cell growth being significantly inhibited when the cultivation was performed by adding sea salt in a stepwise manner. This effect was confirmed significantly in a group to which particularly a small amount of sea salt was supplied. For example, in a case where the cultivation was performed by increasing the salt concentration by 0.5% per day in a stepwise manner, the maximum lipid productivity was 223.2 mg/L/d and the lipid content was 59.4%.

The lipid productivity obtained by the gradient method was higher than the lipid productivity obtained by the batch method (158.9 mg/L/g) or the two-stage culture method (183.9 mg/L/d).

In addition, FIG. 19 shows the compositions of fatty acids obtained by the gradient method. In FIG. 19, Batch indicates the compositions of fatty acid obtained by the batch method. Two-stage indicates the composition of fatty acid obtained by the two-stage culture method, and Salinity-gradient indicates the composition of fatty acid obtained by the gradient method.

As shown in FIG. 19, the fatty acid compositions obtained by the gradient method were mainly saturated fatty acids and monovalent unsaturated fatty acids. It was confirmed the fatty acid compositions have the quality suitable for producing biofuels.

Example 3

(Examination of Effects of Cell Growth and Lipid Accumulation in *Chlorella sorokiniana* NIES-2168 Cultured in Culture Medium to Which Sea Salt was Added in Stepwise Manner)

The effectiveness of the gradient method on other marine microalgae was examined using *Chlorella sorokiniana* NIES-2168.

Figure 20:
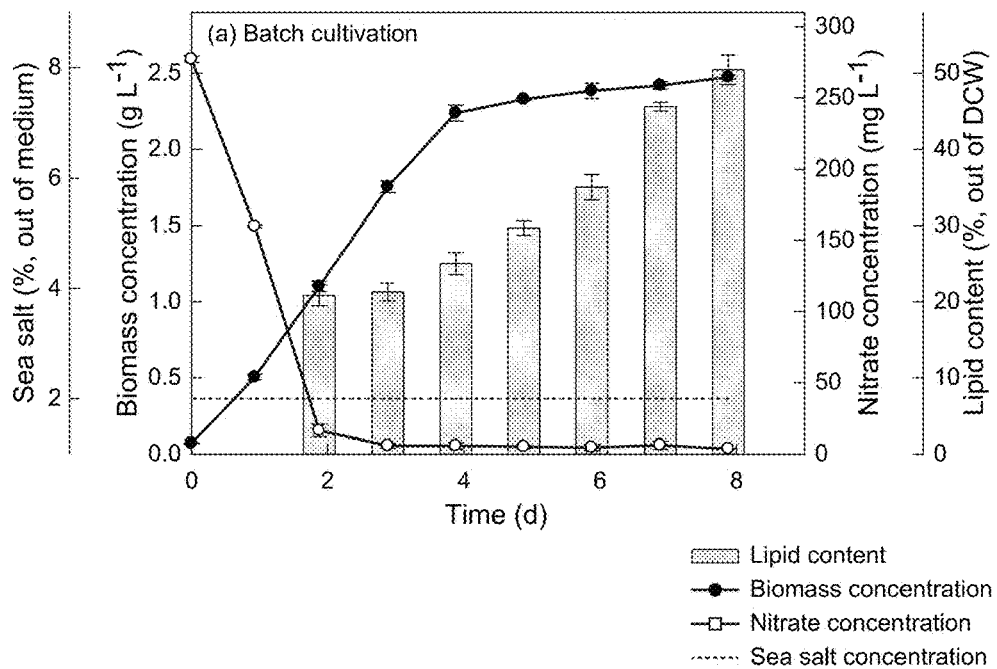
FIG. 20 shows results of time course profiles of the biomass concentration and the lipid content obtained by culturing *Chlorella sorokiniana* NIES-2168 according to a batch method.
Figure 21:
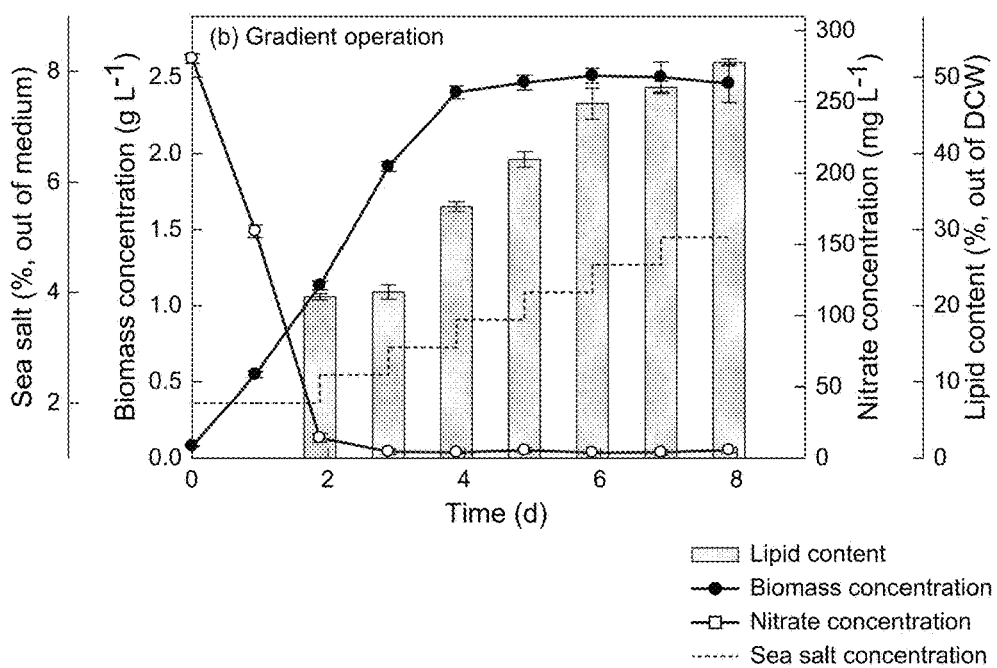
FIG. 21 shows results of time course profiles of the biomass concentration and the lipid content obtained by culturing *Chlorella sorokiniana* NIES-2168 according to the gradient method.

First, the cultivation was performed for approximately 2 days using the modified Bold 3N medium containing 2% of sea salt. Next, after at least 95% of the nitrogen sources were depleted, the cultivation was performed under the condition in which the concentration of salts in the culture solution was allowed to be increased by 0.5% per day in a stepwise manner. The results thereof are shown in FIG. 21. As the control, the cultivation was performed according to the batch method in which the concentration of salts in the culture solution was fixed to 2%. The results are shown in FIG. 20.

As shown in FIG. 21, the lipid productivity of *Chlorella sorokiniana* NIES-2168 was significantly promoted from 139.6 mg/L/d, on the second day of cultivation in which the nitrogen sources were depleted, to 197.8 mg/L/d.

From the results, it was confirmed that the gradient method was also effective for other marine microalgae.

The configurations and combinations thereof in the above-described embodiments are merely examples, and additions, omissions, substitutions, and other modifications of the configurations are possible within the range not departing from the scope of the present invention. Further, the present invention is not limited by the embodiments, but only by the appended claims.

INDUSTRIAL APPLICABILITY

According to the present invention, useful carbon components using algae can be generated with high efficiency.

What is claimed is:

1. A method for producing an oil or fat component, the method comprising:
   culturing salt-tolerant algae belonging to *Chlamydomonas* in a multi-stage culture method with a total number of stages being 3 to 8, wherein the sea salt or sodium chloride concentration of a culture medium in a first stage is in the range of 0.5% by mass to 5% by mass of the total culture medium, and the sea salt or sodium chloride concentration to be increased for each stage after the first stage is in the range of 0.5% by mass to 5% by mass of the total culture medium;
   recovering the salt-tolerant algae; and
   harvesting the oil or fat component from the recovered salt-tolerant algae.

2. The method for producing an oil or fat component according to claim 1, wherein the salt-tolerant algae are cultured in a culture medium of which the sea salt or sodium chloride concentration has been increased by 0.5% by mass to 2% by mass of the total culture medium per day in each stage of the multi-stage culture method.

3. The method for producing an oil or fat component according to claim 1, further comprising:
   performing cultivation under the condition in which the nitrogen content is 10 mg/L or less.

4. The method for producing an oil or fat component according to claim 1, further comprising:
   increasing the sea salt or sodium chloride concentration when a content of nitrate in the culture medium in the first stage becomes 10 mg/L or less in a case where the content thereof at a wavelength of 220 nm is measured.

5. The method for producing an oil or fat component according to claim 1, wherein the culture medium contains seawater, concentrated seawater, or artificial seawater.

6. The method for producing an oil or fat component according to claim 1, wherein the total number of stages being 4 to 6.

7. The method for producing an oil or fat component according to claim 1, wherein the sea salt or sodium chloride concentration of the culture medium in the first stage is in the range of 0.5% by mass to 2% by mass of the total culture medium.

8. The method for producing an oil or fat component according to claim 1, wherein a cultivation period in each stage is in the range of 1 day to 3 days.

9. The method for producing an oil or fat component according to claim 1, wherein the salt-tolerant algae are cultured in a culture medium of which the sea salt or sodium chloride concentration has been increased by 0.5% by mass to 1.5% by mass of the total culture medium per day in each stage of the multi-stage culture method.

10. The method for producing an oil or fat component according to claim 1, wherein the salt-tolerant algae are *Chlamydomonas* sp. JSC4 (FERM ABP-22266).

11. A method for producing a higher unsaturated fatty acid, the method comprising:
   hydrolyzing an oil/fat component obtained by the method for producing an oil or fat component according to claim 10.

12. A method for producing a higher unsaturated fatty acid, the method comprising:
   hydrolyzing an oil or fat component obtained by the method according to claim 1.

13. The method for producing a higher unsaturated fatty acid according to claim 12, wherein the higher unsaturated fatty acid is oleic acid or linolenic acid.

* * * * *

SEQUENCE LISTING

```
<160> NUMBER OF SEQ ID NOS: 1

<210> SEQ ID NO 1
<211> LENGTH: 495
<212> TYPE: DNA
<213> ORGANISM: Chlamydomonas sp. JSC4

<400> SEQUENCE: 1
tacttagcat ggaataacac gataggactc tggcctatct gttggtctgt gggaccggag      60
taatgattaa gaggggtagg cgggggcatt cgtatcccgt tgtcagaggt gagattcttg     120
gatgtacgga agacaaacat ctgcgaaagc atttgccaag gatactttca ttgatcaagg     180
ggttgggggc ttgaagacgg ttagataccg tcgtagtctc aaccataaac gatgccgact     240
agggattggc agatgttcct ttgatgactc tgccagcacc ttataaggaa tcaaagtttt     300
tgggttccgg ggggagtatg gtcacaacgc tgaaacttga aggaattgac ggaagggcac     360
caccagggcc acaagcctgc ggcttaattt gtctcaacac ggggaaactt accaggtcca     420
gacacgggaa ggattgacag attgagagct ctttcttaat tctgtgggtc gtggtgcatg     480
gccgttctta gttgg                                                      495
```